United States Patent
Fru et al.

(10) Patent No.: US 10,980,249 B2
(45) Date of Patent: Apr. 20, 2021

(54) METHOD FOR IMPROVING THE NUTRITIONAL VALUE OF ANIMAL FEED

(71) Applicants: DSM IP Assets B.V., Heerlen (NL); Novozymes A/S, Bagsvaerd (DK)

(72) Inventors: Fidelis Fru, Kaiseraugst (CH); Aaron Joell Cowiesen, Kaiseraugst (CH); Inge Knap, Kaiseraugst (CH)

(73) Assignees: DSM IP Assets B.V., Heerlen (NL); Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/317,697

(22) PCT Filed: Jun. 29, 2015

(86) PCT No.: PCT/EP2015/064739
§ 371 (c)(1),
(2) Date: Dec. 9, 2016

(87) PCT Pub. No.: WO2015/197871
PCT Pub. Date: Dec. 30, 2015

(65) Prior Publication Data
US 2017/0119017 A1 May 4, 2017

(30) Foreign Application Priority Data

Jun. 27, 2014 (EP) .................................. 14174741
Feb. 16, 2015 (EP) .................................. 15155174

(51) Int. Cl.
| | | |
|---|---|---|
| *A23K 10/14* | (2016.01) | |
| *A23K 20/189* | (2016.01) | |
| *C12N 9/50* | (2006.01) | |
| *C12N 9/16* | (2006.01) | |
| *A61K 38/46* | (2006.01) | |
| *A61K 38/48* | (2006.01) | |
| *A61K 38/54* | (2006.01) | |

(52) U.S. Cl.
CPC ............ *A23K 10/14* (2016.05); *A23K 20/189* (2016.05); *A61K 38/465* (2013.01); *A61K 38/48* (2013.01); *A61K 38/54* (2013.01); *C12N 9/16* (2013.01); *C12N 9/50* (2013.01); *C12Y 301/03026* (2013.01); *C12Y 304/00* (2013.01)

(58) Field of Classification Search
CPC ........ A61K 38/48; A61K 38/465; C12N 9/50; C12N 9/48; C12N 9/16
See application file for complete search history.

(56) References Cited

U.S. PATENT DOCUMENTS

| | | | |
|---|---|---|---|
| 5,612,055 | A | 3/1997 | Bedford |
| 5,989,600 | A | 11/1999 | Nielsen et al. |
| 6,139,902 | A | 10/2000 | Kondo et al. |
| 7,217,433 | B2 | 5/2007 | Hansen |
| 8,357,408 | B2 * | 1/2013 | Lassen ................... A23J 3/346 426/53 |
| 2001/0026797 | A1 | 10/2001 | Sjoeholm |
| 2002/0037571 | A1 | 3/2002 | Nagashima et al. |
| 2003/0206913 | A1 | 11/2003 | Webel |
| 2012/0201923 | A1 | 8/2012 | Haefner et al. |
| 2012/0321747 | A1 | 12/2012 | Lassen et al. |
| 2013/0330307 | A1 | 12/2013 | Millan |

FOREIGN PATENT DOCUMENTS

| | | |
|---|---|---|
| EP | 0420358 A1 | 4/1991 |
| EP | 0684313 A2 | 11/1995 |
| JP | 2000-199734 | 7/2000 |
| WO | 95/28850 A1 | 11/1995 |
| WO | 97/35017 A1 | 9/1997 |
| WO | 98/28408 A1 | 7/1998 |
| WO | 98/28409 A1 | 7/1998 |
| WO | 99/08539 A1 | 2/1999 |
| WO | 00/71728 A1 | 11/2000 |
| WO | 01/58276 A2 | 8/2001 |
| WO | 01/90333 A2 | 11/2001 |
| WO | 02/095003 A2 | 11/2002 |
| WO | 03/037102 A2 | 5/2003 |
| WO | 03/066847 A2 | 8/2003 |
| WO | 2004/072221 A2 | 8/2004 |
| WO | 2004/085638 A1 | 10/2004 |
| WO | 2004/111220 A1 | 12/2004 |
| WO | 2004/111221 A1 | 12/2004 |
| WO | 2005/123911 A2 | 12/2005 |
| WO | 2006/028684 A2 | 3/2006 |
| WO | 2006/037327 A2 | 4/2006 |
| WO | 2006/037328 A1 | 4/2006 |
| WO | 2006/038062 A1 | 4/2006 |
| WO | 2006/038128 A2 | 4/2006 |
| WO | 2006/043178 A2 | 4/2006 |
| WO | 2007/112739 A1 | 10/2007 |
| WO | 2008/017066 A2 | 2/2008 |
| WO | 2008/092901 A2 | 8/2008 |
| WO | 2008/097619 A2 | 8/2008 |
| WO | 2008/097620 A1 | 8/2008 |
| WO | 2008/116878 A1 | 10/2008 |
| WO | 2009/129489 A2 | 10/2009 |
| WO | 2010/034835 A2 | 4/2010 |
| WO | 2012/110777 A2 | 8/2012 |
| WO | 2012/143861 A1 | 10/2012 |
| WO | 2012/143862 A1 | 10/2012 |
| WO | 2013/026796 A1 | 2/2013 |
| WO | 2013/098185 A1 | 7/2013 |
| WO | 2013/110766 A1 | 8/2013 |

(Continued)

OTHER PUBLICATIONS

Reuter "Supplement Conversion Ratio" BEEF Nov. 3, 2009, 2pgs (Year: 2009).*

(Continued)

*Primary Examiner* — Thane Underdahl
(74) *Attorney, Agent, or Firm* — Elias Labiris

(57) ABSTRACT

The invention relates to the use of at least one bacterial phytase in combination with one or more protease(s) in animal feed for improving weight gain and/or Feed Conversion Ratio (FCR), wherein the phytase is administered in one or more of the following amounts (dosage ranges): 1,000 FYT/kg feed, 2,000 FYT/kg feed 3,000 FYT/kg feed and wherein the protease is administered in one of the following amounts (dosage ranges): 10,000 units/kg feed, 11,000, 12,000, 13,000, 14,000, 15,000, 16,000, 17,000, 18,000, 19,000, 20,000 units/kg feed.

14 Claims, No Drawings
Specification includes a Sequence Listing.

(56) References Cited

FOREIGN PATENT DOCUMENTS

| WO | 2013/189972 A2 | 12/2013 |
|---|---|---|
| WO | 2014/037438 A1 | 3/2014 |
| WO | 2014/096259 A1 | 6/2014 |
| WO | 2014/122161 A2 | 8/2014 |
| WO | 2014/164442 A1 | 10/2014 |

OTHER PUBLICATIONS

USPTO Sequence Search of claimed SEQ ID No. 29, "Result 3", 2 pages Apr. 18, 2018 (Year: 2018).*
Cowieson et al., Poultrey Science, vol. 84, No. 12, pp. 1860-1867 (2005).
Ehrlich et al., Biochemical and Biophysical Research Communications, vol. 195, No. 1, pp. 53-57 (1993).
Ehrlich et al., SwissProt Accession No. P34754 (1994).
Pasamontes et al., Biochimica et Biophysica Acta, vol. 1353, pp. 217-223 (1997).
Pasamontes et al., SwissProt Accession No. O00093 (1998).
Piddington et al., Gene, vol. 133, pp. 55-62 (1993).
Piddington et al., SwissProt Accession No. P34753 (1994).
Piddington et al., SwissProt Accession No. P34755 (1994).
Van Hartingsveldt et al., Gene, vol. 127, pp. 87-94 (1993).
Van Hartingsveldt et al., SwissProt Accession No. P34752 (1994).
Angel et al., Poultry Science, vol. 90, pp. 2281-2286 (2011).
Anonymous, The EFSA Journal, vol. 1156, pp. 1-25 (2009).
Anonymous, The EFSA Journal, vol. 1185, pp. 1-15 (2009).
Wan et al., Journal of China Agricultural University, vol. 14, No. 5, pp. 80-85 (2009).

* cited by examiner

METHOD FOR IMPROVING THE NUTRITIONAL VALUE OF ANIMAL FEED

CROSS-REFERENCE TO RELATED APPLICATIONS

This application is a 35 U.S.C. 371 national application of international application no. PCT/EP2015/064739 filed Jun. 29, 2015, which claims priority or the benefit under 35 U.S.C. 119 of European application nos. 14174741.0 and 15155174.4 filed Jun. 27, 2014 and Feb. 16, 2015, respectively. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to a method for improving the nutritional value of animal feed. More specifically, the invention relates to a method for improving feed conversion ratio (FCR) of animal feed, which method comprises treating the animal feed source with a high dose of at least one phytase in combination with a proteolytic enzyme.

The invention furthermore relates to feed additive compositions comprising at least one superdosed phytase together one or more proteolytic enzyme, i.e. protease.

SUMMARY OF THE INVENTION

The present invention relates to a method for increasing weight gain and/or improving Feed Conversion Ratio of farm animals, the method comprising the step of applying to the animal a feed with an efficient amount of one or more proteolytic enzymes in combination with at least one phytase wherein:
 a. the phytase is administered in such amounts that the specific activity in the final feed is between 1000 FYT/kg feed and 4000 FYT/kg feed and
 b. the protease is administered in a dosage of between 10,000 units/kg feed and 30,000 units/kg feed.

The invention also relates to the use of one or more proteolytic enzymes in combination with at least one phytase in animal feed for increasing weight gain and/or improving Feed Conversion Ratio of farm animals, wherein:
 a. the phytase is administered in such amounts that the specific activity in the final feed is between 1000 FYT/kg feed and 4000 FYT/kg feed and
 b. the protease is administered in a dosage of between 10,000 units/kg feed and 30,000 units/kg feed.

Overview of Sequence Listing

SEQ ID NO: 1 is the mature amino acid sequence of the AppA phytase from *E. Coli*.
SEQ ID NO: 2 is the mature amino acid sequence of the AppA2 phytase from *E. Coli*.
SEQ ID NO: 3 is the mature amino acid sequence of a phytase derived from *E. Coli*.
SEQ ID NO: 4 is the mature amino acid sequence of a phytase derived from *E. Coli*.
SEQ ID NO: 5 is the mature amino acid sequence of a phytase derived from *E. Coli*.
SEQ ID NO: 6 is the mature amino acid sequence of a phytase disclosed as SEQ ID NO: 1 of WO2008/017066.
SEQ ID NO: 7 is the mature amino acid sequence of a phytase disclosed as SEQ ID NO: 3 of WO2014/164442.
SEQ ID NO: 8 is the mature amino acid sequence of a phytase disclosed as SEQ ID NO: 6 of WO2014/164442.
SEQ ID NO: 9 is the mature amino acid sequence of a phytase disclosed as SEQ ID NO: 8 of WO2014/164442.
SEQ ID NO: 10 is the mature amino acid sequence of a phytase from *Citrobacter braakii* ATCC 51113.
SEQ ID NO: 11 is the mature amino acid sequence of a phytase from *Citrobacter gillenii*.
SEQ ID NO: 12 is the mature amino acid sequence of a phytase from *Citrobacter amalonaticus*.
SEQ ID NO: 13 is the mature amino acid sequence of a phytase from *Citrobacter braakii* YH-15.
SEQ ID NO: 14 is the mature amino acid sequence of a phytase from *Citrobacter freundii* P3-42.
SEQ ID NO: 15 is the mature amino acid sequence of a phytase from *Buttiauxella* sp P1-29.
SEQ ID NO: 16 is the mature amino acid sequence of a phytase from *Buttiauxella* sp P1-29.
SEQ ID NO: 17 is the mature amino acid sequence of a phytase disclosed as SEQ ID NO: 1 of WO2008/097619.
SEQ ID NO: 18 is the mature amino acid sequence of a phytase from *Buttiauxella gaviniae* DSM18930.
SEQ ID NO: 19 is the mature amino acid sequence of a phytase from *Buttiauxella agrestis* DSM18931.
SEQ ID NO: 20 is the mature amino acid sequence of a phytase from *Buttiauxella agrestis* DSM18932.
SEQ ID NO: 21 is the mature amino acid sequence of a phytase from *Peniophora lycii* CBS No. 686.96.
SEQ ID NO: 22 is the mature amino acid sequence of a phytase variant of *Peniophora lycii* CBS No. 686.96.
SEQ ID NO: 23 is the mature amino acid sequence of a phytase from *Hafnia alvei*.
SEQ ID NO: 24 is the mature amino acid sequence of a phytase from *Hafnia* sp. LU11047.
SEQ ID NO: 25 is the mature amino acid sequence of a fusion phytase disclosed as SEQ ID NO: 18 of WO2011/048046.
SEQ ID NO: 26 is the mature amino acid sequence of a fusion phytase variant disclosed as SEQ ID NO: 24 of WO2012/143862.
SEQ ID NO: 27 is the amino acid sequence of a protease from *Nocardiopsis dassonvillei* subsp. *dassonvillei* DSM 43235.
SEQ ID NO: 28 is the mature amino acid sequence of a protease from *Bacillus clausii*.
SEQ ID NO: 29 is the amino acid sequence of a protease from *Nocardiopsis* sp. DSM 16424.
SEQ ID NO: 30 is the amino acid sequence of a protease from *Nocardiopsis alba* DSM 15647.
SEQ ID NO: 31 is the amino acid sequence of a protease from *Nocardiopsis dassonvillei* subsp. *dassonvillei* DSM 43235.
SEQ ID NO: 32 is the mature amino acid sequence of a protease from *Nocardiopsis* sp. NRRL 18262.
SEQ ID NO: 33 is the amino acid sequence of a protease from *Nocardiopsis prasina* DSM 15648.
SEQ ID NO: 34 is the amino acid sequence of a protease from *Nocardiopsis prasina* DSM 15649.
SEQ ID NO: 35 is the amino acid sequence of a protease from *Nocardiopsis prasina* DSM 15649.

SEQ ID NO: 36 is the amino acid sequence of a protease from *Nocardiopsis prasina* DSM 14010.

SEQ ID NO: 37 is the amino acid sequence of a protease from *Nocardiopsis alkaliphila* DSM 44657.

SEQ ID NO: 38 is the amino acid sequence of a protease from *Nocardiopsis lucentensis* DSM 44048.

SEQ ID NO: 39 is the mature amino acid sequence of a protease from *Kribella solani*.

SEQ ID NO: 40 is the mature amino acid sequence of a protease from *Kribella aluminosa*.

SEQ ID NO: 41 is the mature amino acid sequence of a protease from *Saccharomonospora viridis*.

SEQ ID NO: 42 is the mature amino acid sequence of a protease from *Saccharothrix australiensis*.

SEQ ID NO: 43 is the mature amino acid sequence of a protease from *Saccharopolyspora erythraea*.

SEQ ID NO: 44 is the mature amino acid sequence of a protease from *Bacillus* sp NN019138.

SEQ ID NO: 45 is the mature amino acid sequence of a protease from *Saccharopolyspora erythraea*.

SEQ ID NO: 46 is the mature amino acid sequence of a protease from *Meripilus giganteus*.

SEQ ID NO: 47 is the mature amino acid sequence of a protease from *Dactylosporangium variesporum*.

SEQ ID NO: 48 is the mature amino acid sequence of a protease variant from *Bacillus amyloliquefaciens*.

DETAILED DESCRIPTION OF THE INVENTION

It has been found surprisingly that the addition of at least one phytase as defined hereineafter to animal feed, results in a significant improvement of weight gain and/or FCR if the phytase is supplemented in high dosage and combined with a proteolytic enzyme.

Thus in one aspect, the invention relates to a method for increasing weight gain and/or improving Feed Conversion Ratio of farm animals, the method comprising the step of applying to the animal a feed with an efficient amount of one or more proteolytic enzymes in combination with at least one phytase wherein:

a. the phytase is administered in such amounts that the specific activity in the final feed is between 1000 FYT/kg feed and 4000 FYT/kg feed and b. the protease is administered in a dosage of between 10,000 units/kg feed and 30,000 units/kg feed.

The Feed Conversion Ratio (FCR) is indicative of how effectively a feed is utilized. The lower the FCR, the better the feed is utilized. The FCR may be determined on the basis of an animal trial comprising a first treatment in which the phytase and protease for use according to the invention are added to the animal feed in a desired concentration (e.g., 6 or 30 mg enzyme protein per kg feed), and a second treatment (control) with no addition of the enzymes to the animal feed. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%. In further particular embodiments, the FCR is improved (i.e. reduced) as compared to the control by at least 2.6%, 2.7%, 2.8%, 2.9%, or at least 3.0%. In still further particular embodiments, the FCR is improved (i.e., reduced) as compared to the control by at least 3.1%, 3.2%, 3.3%, 3.4%, 3.5%, 3.6%, 3.7%, 3.8%, 4.0%, 4.5%, 5.0%, 5.5%, 6.0%, 6.5%, 7.0% or at least 8.0%. In other particular embodiments, the FCR is improved (i.e. reduced) as compared to the control by between 1.0% and 15.0%, preferably between 1.5% and 12.0%, 2.0% and 11.0%, 2.5% and 11.0%, 3.0% and 10.5%, 4.0% and 10.5% or between 5.0% and 10.0%.

In another embodiment, the FCR is improved (i.e. reduced) as compared to using the phytase at the same dose alone by at least 1.0%, preferably at least 1.5%, 2.0%, 2.5%, 3.0%, 3.5%, 4.0%, 4.5%, 5.0%, 5.5%, 6.0%, 6.5%, 7.0% or at least 8.0%. In other particular embodiments, the FCR is improved (i.e. reduced) as compared to using the phytase at the same dose alone by between 1.0% and 15.0%, preferably between 1.5% and 12.0%, 2.0% and 11.0%, 2.25% and 11.0%, 2.5% and 10.5%, 2.75% and 10.5% or between 3.0% and 10.0%.

An improved weight gain means an improved daily, weekly, bi-weekly, or monthly weight gain (in g or kg per the relevant time period), relative to a control without added phytase and protease.

Phytases

Phytases (myo-inositol hexakisphosphate phosphohydrolases; EC 3.1.3.8) are enzymes that hydrolyze phytate (myo-inositol hexakisphosphate) to myo-inositol and inorganic phosphate and are known to be valuable feed additives.

A variety of Phytases differing in pH optima, substrate specificity, and specificity of hydrolysis have been identified in plants and fungi. Acid Phytases from wheat bran and Aspergilli have been extensively studied and the stereo specificity of hydrolysis has been well established. Based on the specificity of initial hydrolysis, two classes of acid Phytases are recognized by the International Union of Pure and Applied Chemistry and the International Union of Biochemistry (IUPAC-IUB, 1975), the 6-Phytase, found for example in plants, and the 3-Phytase, found in fungi. The 6-Phytase hydrolyses the phosphate ester at the L-6 (or D-4) position of phytic acid, and the 3-Phytase hydrolyses the phosphate ester at the D-3 position.

The ENZYME site at the internet (http://www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The ENZYME database, 2000, Nucleic Acids Res 28:304-305). See also the handbook Enzyme Nomenclature from NC-IUBMB, 1992).

According to the ENZYME site, two different types of phytases are known: A so-called 3-phytase (myo-inositol hexaphosphate 3-phosphohydrolase, EC 3.1.3.8) and a so-called 6-phytase (myo-inositol hexaphosphate 6-phosphohydrolase, EC 3.1.3.26). For the purposes of the present invention, both types are included in the definition of phytase.

Examples of ascomycete phytases are those derived from a strain of *Aspergillus*, for example *Aspergillus awamori* PHYA (SWISSPROT P34753, Gene 133:55-62 (1993)), *Aspergillus niger (ficuum)* PHYA (SWISSPROT P34752, EP420358, Gene 127:87-94 (1993)), *Aspergillus awamori* PHYB (SWISSPROT P34755, Gene 133:55-62 (1993)), *Aspergillus niger* PHYB (SWISSPROT P34754, Biochem. Biophys. Res. Commun. 195:53-57(1993)); or a strain of *Emericella*, for example *Emericella nidulans* PHYB (SWISSPROT 000093, Biochim. Biophys. Acta 1353:217-223 (1997)); or a strain of *Thermomyces* (*Humicola*), for example the *Thermomyces lanuginosus* phytase described in WO 97/35017. Other examples of ascomycete phytases are disclosed in EP 684313 (for example derived from strains of *Aspergillus fumigatus*, *Aspergillus terreus*, and *Myceliophthora thermophila*); JP 11000164 (a phytase derived from a strain of *Penicillium.*); U.S. Pat. No. 6,139,902 (a phytase derived from a strain of *Aspergillus*), and WO 98/13480 (*Monascus anka* phytase).

Examples of basidiomycete phytases are the phytases derived from *Paxillus involutus, Trametes pubescens, Agrocybe pediades* and *Peniophora lycii* (see WO 98/28409).

In the present context, a preferred Phytase according to the invention is classified as belonging to the EC 3.1.3.26 group. The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web at http://www.chem.gmw.ac.uk/iubmb/enzyme/index.html.

Examples of Phytases for use according to the present inventions are:

Phytases derived from strains of *E coli*, from strains of *Buttiauxella*, Ascomycete Phytases as disclosed in EP 684313 (for example derived from strains of *Aspergillus fumigatus, Aspergillus terreus*, and *Myceliophthora thermophila*); JP 11000164 (a Phytase derived from a strain of *Penicillium.*); U.S. Pat. No. 6,139,902 (a Phytase derived from a strain of *Aspergillus*), WO 98/13480 (*Monascus anka* Phytase), WO 2008/116878 and WO 2010/034835 (*Hafnia* phytase).

A preferred phytase for use according to the invention is derived from the family Enterobacteriaceae, and more preferably is a species of *Escherichia, Citrobacter, Buttiauxella* or *Hafnia*.

Preferred examples of *Escherichia* species are *Escherichia coli* such as those disclosed in WO 2000/71728, WO 2001/90333, WO 2002/095003, WO 2002/095003, WO 2006/028684, WO 2006/028684, WO 1999/08539 and WO 2003/037102 or variants thereof, such as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. Preferred examples of *Citrobacter* are *Citrobacter amalonaticus, C. farmer, C. freundii, C. gillenii, C. intermedius, C. koseri* and *C. rodentium*, such as those disclosed in WO 2004/085638, WO 2006/037327, WO 2006/037328, WO 2006/038062, WO 2006/038128 and WO 2007/112739 or variants thereof, such as SEQ ID NO: 10, SEQ ID NO: 11, SEQ ID NO: 12, SEQ ID NO: 13 and SEQ ID NO: 14. Preferred examples of *Hafnia* are *Hafnia alvei* and *H. paralvei* such as those disclosed in WO 2008/116878, WO 2010/034835, WO 2011/048046, WO 2012/143861 and WO 2012/143862 or variants thereof, such as SEQ ID NO: 23, SEQ ID NO: 24, SEQ ID NO: 25 and SEQ ID NO: 26. Preferred examples of *Buttiauxella* are *Buttiauxella agrestis, B. brennerae, B. ferragutiae, B. gaviniae, B. izardii, B. noackiae* and *B. warmboldiae* such as those disclosed in WO 2006/043178, 2008/092901, WO 2008/097619, WO 2008/097620, WO 2009/129489 or variants thereof, such as SEQ ID NO: 15, SEQ ID NO: 16, SEQ ID NO: 17, SEQ ID NO: 18, SEQ ID NO: 19 and SEQ ID NO: 20.

In another preferred embodiment, the phytase for use according to the invention is derived from the family Peniophoraceae and more preferably is a species of *Peniophora*, such as those disclosed in WO 1998/028408, WO 1998/028409 and WO 2003/066847 or variants thereof, such as SEQ ID NO: 21 and SEQ ID NO: 22.

Examples of *Peniophora* species are: *Peniophora aurantiaca, P. cinerea, P. decorticans, P. duplex, P. ericsonii, P. incamate, P. lycii, P. meridionalis, P. nuda, P. piceae, P. pini, P. pithya, P. polygonia, P. proxima, P. pseudo-pini, P. rufa, P. versicolor*, and species simply classified as *Peniophora* sp. A preferred species is *Peniophora lycii*. A preferred strain is *Peniophora lycii* CBS 686.96.

In a preferred embodiment, the amino acid sequence of the phytase has at least 70% sequence identity to the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26. In a more preferred embodiment, the amino acid sequence of the phytase has at least 80% sequence identity to the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26. In an even more preferred embodiment, the amino acid sequence of the phytase has at least 90% sequence identity to the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26. In an even more preferred embodiment, the amino acid sequence of the phytase has at least 95%, such as at least 96%, at least 97%, at least 98%, or at least 99% sequence identity to the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

For purposes of the present invention, preferred phytases are the phytases contained in the following commercial products: Ronozyme®HiPhos, Ronozyme®NP and Ronozyme® P (DSM Nutritional Products AG), Natuphos™ (BASF), Finase® and Quantum® Blue (AB Enzymes), OptiPhos® (Huvepharma) Phyzyme® XP (Verenium/DuPont) and Axtra® PHY (DuPont).

For the purpose of the present invention, phytase activity is determined by the liberation of inorganic phosphate from Na-phytate solution, wherein one phytase activity unit is the amount of enzyme which liberates 1 µmol inorganic phosphate per min from a 0.0051 M Na-phytate solution in 0.25 M Na-acetate, pH 5.5 and at 37° C. (Engelen, A. J., et al., 1994, "Simple and rapid determination of phytase activity", *J. AOAC Int.* 77:760-764). Examples of activity unit names are: FYT, FTU and U. Phytase activity may be determined using the assay as described in Example 1 ("Determination of phytase activity"). In one aspect, the polypeptides of the present invention have at least 20%, e.g., at least 40%, at least 50%, at least 60%, at least 70%, at least 80%, at least 90%, at least 95%, or at least 100% of the phytase activity of SEQ ID NO: 10.

Specific activity is measured on highly purified samples (an SDS poly acryl amide gel should show the presence of only one component). The enzyme protein concentration may be determined by amino acid analysis, and the phytase activity in the units of FYT. Specific activity is a characteristic of the specific phytase variant in question, and it is calculated as the phytase activity measured in FYT units per mg phytase enzyme protein.

For determining mg Phytase protein per kg feed or feed additive, the enzyme is purified from the feed composition or the feed additive, and the specific activity of the purified enzyme is determined using a relevant assay. The Phytase activity of the feed composition or the feed additive is also determined using the same assay, and on the basis of these two determinations, the dosage in mg Phytase protein per kg feed is calculated.

According to the invention, the phytase should of course be applied in an effective amount, i.e. in an amount adequate for improving nutritional value of feed if it is used in combination with a proteolytic enzyme [obtaining the desired effect, e.g. improving FCR]. It is at present contemplated that the phytase is administered in such amounts that the specific activity in the final feed is between 1000 FYT/kg feed and 4000 FYT/kg feed. In particular embodiments, the specific activity is at least 1100, 1200, 1300, 1400, 1500, 1600, 1700, 1800, 1900, 2000, 2100, 2200, 2300, 2400, 2500, 2600, 2700, 2800, 2900 or at least 3000 FYT/kg feed. In another particular embodiment, the specific activity is between 1200 and 3900 FYT/kg feed, preferably between 1400 and 3800 FYT/kg feed, between 1600 and 3700 FYT/kg feed, between 1800 and 3600 FYT/kg feed, between 1900 and 3500 FYT/kg feed, between 2000 and 3500 FYT/kg feed, between 2200 and 3500 FYT/kg feed, between 2400 and 3500 FYT/kg feed, between 2500 and 3500 FYT/kg feed, between 2600 and 3400 FYT/kg feed, between 2700 and 3300 FYT/kg feed and between 2800 and 3200 FYT/kg feed.

In a preferred embodiment, the phytase is applied at between 2 and 4 times standard commercial dose for that phytase.

Proteases

Proteolytic enzymes or proteases, or peptidases, catabolize peptide bonds in proteins breaking them down into fragments of amino acid chains, or peptides.

Proteases are classified on the basis of their catalytic mechanism into the following groups: serine proteases (S), cysteine proteases (C), aspartic proteases (A), metalloproteases (M), and unknown, or as yet unclassified, proteases (U), see Handbook of Proteolytic Enzymes, A. J. Barrett, N. D. Rawlings, J. F. Woessner (eds), Academic Press (1998), in particular the general introduction part.

Proteases for use according to the invention are acid stable proteases, preferably acid stable serine proteases. In a further preferred embodiment, the acid stable serine proteases are S1 serine proteases. Acid stability may be determined using the kinetic Suc-AAPF-pNA assay as described in example 2 of WO 01/58276 and a protease is considered to be acid stable if there is >50% residual activity at pH 3 compared to the activity to samples which were kept at stable conditions (5° C. and the optimal pH for that protease).

In a particular embodiment, the protease for use according to the invention is a microbial protease, the term microbial indicating that the protease is derived from, or originates from a microorganism, or is an analogue, a fragment, a variant, a mutant, or a synthetic protease derived from a microorganism. It may be produced or expressed in the original wild-type microbial strain, in another microbial strain, or in a plant; i. e. the term covers the expression of wild-type, naturally occurring proteases, as well as expression in any host of recombinant, genetically engineered or synthetic proteases.

Examples of microorganisms are bacteria, e. g. bacteria of the phylum Actinobacteria, e. g. of the class Actinobacteria, e.g. of the order Streptosporangiales, e.g. of the family Nocardiopsaceae, e.g. of the genus *Nocardiopsis*, e. g. *Nocardiopsis* sp. NRRL 18262, and *Nocardiopsis alba*; e.g. of the species *Bacillus* or mutants or variants thereof exhibiting protease activity.

Preferred proteases according to the invention are acid stable serine proteases obtained or obtainable from the class Actinobacteria, such as those derived from *Nocardiopsis dassonvillei* subsp. *dassonvillei* DSM 43235 (A1918L1), *Nocardiopsis prasina* DSM 15649 (NN018335L1), *Nocardiopsis prasina* (previously *alba*) DSM 14010 (NN18140L1), *Nocardiopsis* sp. DSM 16424 (NN018704L2), *Nocardiopsis alkaliphila* DSM 44657 (NN019340L2) and *Nocardiopsis lucentensis* DSM 44048 (NN019002L2), as well as homologous proteases. Other preferred proteases are those described in WO 2001/058276, WO 2004/111220, WO 2004/111221, WO 2004/072221, WO 2005/123911, WO 2013/026796, WO 2013/098185, WO 2013/110766, WO 2013/189972, WO 2014/096259, WO 2014/122161 and WO 2014/037438.

The term serine protease refers to serine peptidases and their clans as defined in the above Handbook. In the 1998 version of this handbook, serine peptidases and their clans are dealt with in chapters 1-175. Serine proteases may be defined as peptidases in which the catalytic mechanism depends upon the hydroxyl group of a serine residue acting as the nucleophile that attacks the peptide bond. Examples of serine proteases for use according to the invention are proteases of Clan SA, e. g. Family S2 (Streptogrisin), e. g. Sub-family S2A (alpha-lytic protease), as defined in the above Handbook.

Protease activity can be measured using any assay, in which a substrate is employed, that includes peptide bonds relevant for the specificity of the protease in question. Examples of protease substrates are casein, and pNA-substrates, such as Suc-AAPF-pNA (available e.g. from Sigma S-7388). Another example is Protazyme AK (azurine dyed crosslinked casein prepared as tablets by Megazyme T-PRAK). Example 2 of WO 01/58276 describes suitable protease assays. A preferred assay is the Protazyme assay of Example 2D (the pH and temperature should be adjusted to the protease in question as generally described previously).

There are no limitations on the origin of the acid stable serine protease for use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e. g. by Site-directed Mutagenesis, by PCR (using a PCR fragment containing the desired mutation as one of the primers in the PCR reactions), or by Random Mutagenesis. The preparation of consensus proteins is described in e. g. EP 0 897 985.

In a preferred embodiment, the amino acid sequence of the protease has at least 70% sequence identity to the polypeptide of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or SEQ ID NO: 48. In a more preferred embodiment, the amino acid sequence of the protease has at least 80% sequence identity to the polypeptide of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or SEQ ID NO: 48. In an even more preferred embodiment, the amino acid sequence of the protease has at least 90% sequence identity to the polypeptide of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or SEQ ID NO: 48. In an even more preferred embodiment, the amino acid sequence of the protease has at least 95%, such as at least 96%, at least 97%, at least 98%, or at least 99% sequence identity to the polypeptide of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or SEQ ID NO: 48.

For calculating percentage identity, any computer program known in the art can be used. Examples of such computer programs are the Clustal V algorithm (Higgins, D. G., and Sharp, P. M. (1989), Gene (Amsterdam), 73, 237-244; and the GAP program provided in the GCG version 8 program package (Program Manual for the Wisconsin Package, Version 8, Genetics Computer Group, 575 Science Drive, Madison, Wis., USA 53711) (Needleman, S. B. and Wunsch, C. D., (1970), Journal of Molecular Biology, 48, 443-453.

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment).

In another particular embodiment, the protease for use according to the invention, besides being acid-stable, is also thermostable.

The term thermostable means for proteases one or more of the following: That the temperature optimum is at least 50° C., 52° C., 54° C., 56° C., 58° C., 60° C., 62° C., 64° C., 66° C., °68 C, or at least °70 C.

A commercially available serine proteases derived from *Nocardiopsis* is Ronozyme®ProAct® (DSM Nutritional Products AG).

In the use according to the invention it is at present contemplated that the protease is administered in a dosage of between 5,000 units/kg feed and 30,000 units/kg feed, preferably between 7,000 units/kg feed and 28,000 units/kg feed, between 8,000 units/kg feed and 26,000 units/kg feed, between 9,000 units/kg feed and 24,000 units/kg feed, between 10,000 units/kg feed and 22,000 units/kg feed, between 11,000 units/kg feed and 20,000 units/kg feed, between 12,000 units/kg feed and 18,000 units/kg feed, or between 13,000 units/kg feed and 17,000 units/kg feed, or for example in one of the following amounts (dosage ranges): 5,000 units/kg feed, 7,000, 8,000, 9,000, 10,000, 11,000, 12,000, 13,000, 14,000, 15,000, 16,000, 17,000, 18,000, 19,000, 20,000, 22,000, 24,000, 26,000, 28,000, 30,000 units/kg feed. One protease unit (PROT) is the amount of enzyme that releases 1 µmol of p-nitroaniline from 1 mM substrate (Suc-Ala-Ala-Pro-Phe-pnA) per minute at pH 9.0 and 37° C.

Phytase and Protease Combinations

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
 a. the phytase is administered in such amounts that the specific activity in the final feed is between 1000 FYT/kg feed and 4000 FYT/kg feed and
 b. the protease is administered in a dosage of between 10,000 units/kg feed and 30,000 units/kg feed.

In an embodiment, the monogastric animal is selected from the group consisting of pigs, swine (including, but not limited to, piglets, growing pigs, and sows); poultry, turkeys, ducks, quail, guinea fowl, geese, pigeons (including squabs) and chicken (broilers, chicks, layers). In a preferred embodiment the monogastric animal is selected from the group consisting of chicken, broilers, chicks and layers.

In a preferred embodiment, the phytase is applied at between 2 and 4 times standard commercial dose for that phytase.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
 a. the phytase is derived from the family Enterobacteriaceae and is administered in such amounts that the specific activity in the final feed is between 1000 FYT/kg feed and 4000 FYT/kg feed and
 b. the protease is an acid stable serine protease derived from the class Actinobacteria and is administered in a dosage of between 10,000 units/kg feed and 30,000 units/kg feed.

In a preferred embodiment, the phytase is applied at between 2 and 4 times standard commercial dose for that phytase.

In an embodiment, the monogastric animal is selected from the group consisting of pigs, swine (including, but not limited to, piglets, growing pigs, and sows); poultry, turkeys, ducks, quail, guinea fowl, geese, pigeons (including squabs) and chicken (broilers, chicks, layers). In a preferred embodiment the monogastric animal is selected from the group consisting of chicken, broilers, chicks and layers.

In an embodiment, the phytase is derived from the family Enterobacteriaceae and the acid stable serine protease is derived from the family Nocardiopsaceae, preferably the genus *Nocardiopsis*. In an embodiment, the phytase is derived from the genus *Escherichia* and the acid stable serine protease is derived from the genus *Nocardiopsis*. In an embodiment, the phytase is derived from the genus *Citrobacter* and the acid stable serine protease is derived from the genus *Nocardiopsis*. In an embodiment, the phytase is derived from the genus *Buttiauxella* and the acid stable serine protease is derived from the genus *Nocardiopsis*. In an embodiment, the phytase is derived from the genus *Hafnia* and the acid stable serine protease is derived from the genus *Nocardiopsis*.

In another embodiment, the phytase is derived from the family Enterobacteriaceae and the acid stable serine protease is derived from the family Pseudonocardiaceae. In another embodiment, the phytase is derived from the family Enterobacteriaceae and the acid stable serine protease is derived from the family Micromonosporaceae. In another embodiment, the phytase is derived from the family Enterobacteriaceae and the acid stable serine protease is derived from the family Nocardioidaceae. In another embodiment, the phytase is derived from the family Enterobacteriaceae and the acid stable serine protease is derived from the family Bacillaceae, preferably the genus *Bacillus*.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the family Peniophoraceae and is administered in such amounts that the specific activity in the final feed is between 1000 FYT/kg feed and 4000 FYT/kg feed and
  b. the protease is an acid stable serine protease derived from the class Actinobacteria and is administered in a dosage of between 10,000 units/kg feed and 30,000 units/kg feed.

In a preferred embodiment, the phytase is applied at between 2 and 4 times standard commercial dose for that phytase.

In an embodiment, the monogastric animal is selected from the group consisting of pigs, swine (including, but not limited to, piglets, growing pigs, and sows); poultry, turkeys, ducks, quail, guinea fowl, geese, pigeons (including squabs) and chicken (broilers, chicks, layers). In a preferred embodiment the monogastric animal is selected from the group consisting of chicken, broilers, chicks and layers.

In an embodiment, the phytase is derived from the genus *Peniophora* and the acid stable serine protease is derived from the family Nocardiopsaceae, preferably the genus *Nocardiopsis*. In another embodiment, the phytase is derived from the family Peniophoraceae and the acid stable serine protease is derived from the family Peniophoraceae. In another embodiment, the phytase is derived from the family Peniophoraceae and the acid stable serine protease is derived from the family Micromonosporaceae. In another embodiment, the phytase is derived from the family Peniophoraceae and the acid stable serine protease is derived from the family Nocardioidaceae. In another embodiment, the phytase is derived from the family Peniophoraceae and the acid stable serine protease is derived from the family Bacillaceae, preferably the genus *Bacillus*.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the family Enterobacteriaceae and is administered in such amounts that the specific activity in the final feed is between 1000 FYT/kg feed and 4000 FYT/kg feed;
  b. the protease is an acid stable serine protease derived from the class Actinobacteria and is administered in a dosage of between 10,000 units/kg feed and 20,000 units/kg feed; and
  c. the monogastric animal is selected from the group consisting of chicken, broilers, chicks and layers.

In a preferred embodiment, the phytase is applied at between 2 and 4 times standard commercial dose for that phytase.

In an embodiment, the phytase is derived from the family Enterobacteriaceae and the acid stable serine protease is an S1 protease derived from the family Nocardiopsaceae, preferably the genus *Nocardiopsis*. In an embodiment, the phytase is derived from the genus *Escherichia* and the acid stable serine protease is an S1 protease derived from the genus *Nocardiopsis*. In an embodiment, the phytase is derived from the genus *Citrobacter* and the acid stable serine protease is an S1 protease derived from the genus *Nocardiopsis*. In an embodiment, the phytase is derived from the genus *Buttiauxella* and the acid stable serine protease is an S1 protease derived from the genus *Nocardiopsis*. In an embodiment, the phytase is derived from the genus *Hafnia* and the acid stable serine protease is an S1 protease derived from the genus *Nocardiopsis*.

In another embodiment, the phytase is derived from the family Enterobacteriaceae and the acid stable serine protease is an S8 protease derived from the family Pseudonocardiaceae. In another embodiment, the phytase is derived from the family Enterobacteriaceae and the acid stable serine protease is an S8 protease derived from the family Micromonosporaceae. In another embodiment, the phytase is derived from the family Enterobacteriaceae and the acid stable serine protease is an S8 protease derived from the family Nocardioidaceae. In another embodiment, the phytase is derived from the family Enterobacteriaceae and the acid stable serine protease is derived from the family Bacillaceae, preferably the genus *Bacillus*.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the family Peniophoraceae and is administered in such amounts that the specific activity in the final feed is between 1000 FYT/kg feed and 4000 FYT/kg feed;
  b. the protease is an acid stable serine protease derived from the class Actinobacteria and is administered in a dosage of between 10,000 units/kg feed and 20,000 units/kg feed; and
  c. the monogastric animal is selected from the group consisting of chicken, broilers, chicks and layers.

In a preferred embodiment, the phytase is applied at between 2 and 4 times standard commercial dose for that phytase.

In an embodiment, the phytase is derived from the genus *Peniophora* and the acid stable serine protease is an S1 protease derived from the family Nocardiopsaceae, preferably the genus *Nocardiopsis*. In another embodiment, the phytase is derived from the family Peniophoraceae and the acid stable serine protease is an S1 protease derived from the family Peniophoraceae. In another embodiment, the phytase is derived from the family Peniophoraceae and the acid stable serine protease is an S1 protease derived from the family Micromonosporaceae. In another embodiment, the phytase is derived from the family Peniophoraceae and the acid stable serine protease is an S1 protease derived from the family Nocardioidaceae. In another embodiment, the phytase is derived from the family Peniophoraceae and the acid stable serine protease is an S8 protease derived from the family Bacillaceae, preferably the genus *Bacillus*.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the genus *Citrobacter* and is administered in such amounts that the specific activity in the final feed is between 1500 FYT/kg feed and 3500 FYT/kg feed;
  b. the protease is an acid stable S1 serine protease derived from the genus *Nocardiopsis* and is administered in a dosage of between 10,000 units/kg feed and 20,000 units/kg feed; and
  c. the monogastric animal is selected from the group consisting of chicken, broilers, chicks and layers.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the genus *Buttiauxella* and is administered in such amounts that the specific activity in the final feed is between 1000 FYT/kg feed and 2000 FYT/kg feed;
  b. the protease is an acid stable S1 serine protease derived from the genus *Nocardiopsis* and is administered in a dosage of between 10,000 units/kg feed and 20,000 units/kg feed; and
  c. the monogastric animal is selected from the group consisting of chicken, broilers, chicks and layers.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the genus *Buttiauxella* and is administered in such amounts that the specific activity in the final feed is between 1000 FYT/kg feed and 2000 FYT/kg feed;
  b. the protease is an acid stable S8 serine protease derived from the genus *Bacillus* and is administered in a dosage of between 10,000 units/kg feed and 20,000 units/kg feed; and
  c. the monogastric animal is selected from the group consisting of chicken, broilers, chicks and layers.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the genus *Escherichia* and is administered in such amounts that the specific activity in the final feed is between 1000 FYT/kg feed and 2000 FYT/kg feed;
  b. the protease is an acid stable S8 serine protease derived from the genus *Bacillus* and is administered in a dosage of between 10,000 units/kg feed and 20,000 units/kg feed; and
  c. the monogastric animal is selected from the group consisting of chicken, broilers, chicks and layers.

In a particular embodiment, the invention relates to a method for improving the Feed Conversion Ratio of monogastric animals, the method comprising the step of applying to the monogastric animal a feed with an efficient amount of one or more proteolytic enzymes in combination with at least one phytase wherein:
  a. the phytase is derived from the genus *Escherichia* and is administered in such amounts that the specific activity in the final feed is between 1000 FYT/kg feed and 2000 FYT/kg feed;
  b. the protease is an acid stable S8 serine protease derived from the genus *Bacillus* and is administered in a dosage of between 10,000 units/kg feed and 20,000 units/kg feed; and
  c. the monogastric animal is selected from the group consisting of chicken, broilers, chicks and layers.

Animal Feed

In a particular embodiment, the phytase and the protease, in the form in which they are added to the feed, or when being included in a feed additive, are well-defined. Well-defined means, that the enzyme preparation is at least 50% pure on a protein-basis. In other particular embodiments the enzyme preparation is at least 60, 70, 80, 85, 88, 90, 92, 94, or at least 95% pure. Purity may be determined by any method known in the art, e.g. by SDS-PAGE, or by Size-exclusion chromatography (see Example 12 of WO 01/58275).

A well-defined enzyme preparation is advantageous. For instance, it is much easier to dose correctly to the feed an enzyme that is essentially free from interfering or contaminating other enzymes. The term dose correctly refers in particular to the objective of obtaining consistent and constant results, and the capability of optimising dosage based upon the desired effect.

For the present purposes, the term animal includes all animals, including human beings. In a particular embodiment, the phytase variants and compositions of the invention can be used as a feed additive for non-human animals. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish). In an embodiment, the monogastric animal is selected from the group consisting of swine (including, but not limited to, piglets, growing pigs, and sows); poultry, turkeys, ducks, quail, guinea fowl, geese, pigeons (including squabs) and chicken (broilers, chicks, layers). In a preferred embodiment the monogastric animal is selected from the group consisting of chicken, broilers, chicks and layers.

The term feed or feed composition means any compound, preparation, mixture, or composition suitable for, or intended for intake by an animal. The feed can be fed to the animal before, after, or simultaneously with the diet. The latter is preferred.

The composition of the invention, when intended for addition to animal feed, may be designated an animal feed additive. Such additive always comprises the enzymes in question, preferably in the form of stabilized liquid or dry compositions. The additive may comprise other components or ingredients of animal feed. The so-called pre-mixes for animal feed are particular examples of such animal feed additives. Pre-mixes may contain the enzyme(s) in question, and in addition at least one vitamin and/or at least one mineral.

In a preferred example, the phytase and the protease, which are added to the feed via a feed additive composition, are dosed such that the final feed has the following dosages:

Phytase: at least 2000 FYT/kg feed and Protease: 15,000 units/kg feed, or

Phytase: 3000 FYT/kg feed and Protease: 15,000 units/kg feed.

In another preferred example, the phytase and the protease, which are added to the feed via a feed additive composition, are dosed such that the final feed has the following dosages:

Phytase: 1700 to 2300 FYT/kg feed and Protease: 12,000 to 18,000 units/kg feed, or Phytase: 2700 to 3300 FYT/kg feed and Protease: 12,000 to 18,000 units/kg feed.

Accordingly, in a particular embodiment, in addition to the component polypeptides, the composition of the invention may comprise or contain at least one fat-soluble vitamin, and/or at least one water-soluble vitamin, and/or at least one trace mineral. Also at least one macro mineral may be included.

Examples of fat-soluble vitamins are vitamin A, D3, E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

Further, optional, feed-additive ingredients are colouring agents, aroma compounds, stabilizers, additional enzymes, and antimicrobial peptides.

Additional enzyme components of the composition of the invention include at least one polypeptide having xylanase activity; and/or at least one polypeptide having endoglucanase activity; and/or at least one polypeptide having endo-1,3(4)-beta-glucanase activity.

Xylanase activity can be measured using any assay, in which a substrate is employed, that includes 1,4-beta-D-xylosidic endo-linkages in xylans. Different types of substrates are available for the determination of xylanase activity e.g. Xylazyme cross-linked arabinoxylan tablets (from MegaZyme), or insoluble powder dispersions and solutions of azo-dyed arabinoxylan.

Endoglucanase activity can be determined using any endoglucanase assay known in the art. For example, various cellulose- or beta-glucan-containing substrates can be applied. An endoglucanase assay may use AZCL-Barley beta-Glucan, or preferably (1) AZCL-HE-Cellulose, or (2) Azo-CM-cellulose as a substrate. In both cases, the degradation of the substrate is followed spectrophotometrically at OD595 (see the Megazyme method for AZCL-polysaccharides for the assay of endo-hydrolases at http://www.megazyme.com/booklets/AZCLPOL.pdf.

Endo-1,3(4)-beta-glucanase activity can be determined using any endo-1,3(4)-beta-glucanase assay known in the art. A preferred substrate for endo-1,3(4)-beta-glucanase activity measurements is a cross-linked azo-coloured beta-glucan Barley substrate, wherein the measurements are based on spectrophotometric determination principles.

For assaying xylanase, endoglucanase, beta-1,3(4)-glucanase and protease activity the assay-pH and the assay-temperature are to be adapted to the enzyme in question (preferably a pH close to the optimum pH, and a temperature close to the optimum temperature). A preferred assay pH is in the range of 2-10, preferably 3-9, more preferably pH 3 or 4 or 5 or 6 or 7 or 8, for example pH 3 or pH 7. A preferred assay temperature is in the range of 20-80° C., preferably 30-80° C., more preferably 40-75° C., even more preferably 40-60° C., preferably 40 or 45 or 50° C. The enzyme activity is defined by reference to appropriate blinds, e.g. a buffer blind.

Examples of antimicrobial peptides (AMP's) are CAP18, Leucocin A, Tritrpticin, Protegrin-1, Thanatin, Lactoferrin, Lactoferricin, and Ovispirin such as Novispirin (Robert Lehrer, 2000), and variants or fragments thereof which retain antimicrobial activity. Other examples are anti-fungal polypeptides (AFP's) such as those derived from *Aspergillus giganteus*, and *Aspergillus niger*, as well as variants and fragments thereof which retain antifungal activity, as disclosed in WO 94/01459 and PCT/DK02/00289.

In a particular embodiment, the animal feed additive of the invention is intended for being included (or prescribed as having to be included) in animal diets or feed at levels of 0.0010-12.0%, or 0.0050-11.0%, or 0.0100-10.0%; more particularly 0.05-5.0%; or 0.2-1.0% (% meaning g additive per 100 g feed). This is so in particular for premixes.

Accordingly, the concentrations of the individual components of the animal feed additive, e.g. the premix, can be found by multiplying the final in-feed concentration of the same component by, respectively, 10-10000; 20-2000; or 100-500 (referring to the above three percentage inclusion intervals).

The final in-feed concentrations of important feed components may reflect the nutritional requirements of the animal, which are generally known by the skilled nutritionist, and presented in publications such as the following: NRC, Nutrient requirements in swine, ninth revised edition 1988, subcommittee on swine nutrition, committee on animal nutrition, board of agriculture, national research council. National Academy Press, Washington, D.C. 1988; and NRC, Nutrient requirements of poultry, ninth revised edition 1994, subcommittee on poultry nutrition, committee on animal nutrition, board of agriculture, national research council, National Academy Press, Washington, D.C., 1994.

The composition of the invention can be prepared according to methods known in the art, e.g. by mixing the phytase and the protease with the additional ingredients, if any.

Animal feed compositions or diets have a relatively high content of protein. An animal feed composition according to the invention has a crude protein content of 50-800, or 75-700, or 100-600, or 110-500, or 120-490 g/kg, and furthermore comprises a composition of the invention.

Furthermore, or in the alternative (to the crude protein content indicated above), the animal feed composition of the invention has a content of metabolisable energy of 10-30, or 11-28, or 11-26, or 12-25 MJ/kg; and/or a content of calcium of 0.1-200, or 0.5-150, or 1-100, or 4-50 g/kg; and/or a content of available phosphorus of 0.1-200, or 0.5-150, or 1-100, or 1-50, or 1-25 g/kg; and/or a content of methionine of 0.1-100, or 0.5-75, or 1-50, or 1-30 g/kg; and/or a content of methionine plus cysteine of 0.1-150, or 0.5-125, or 1-80 g/kg; and/or a content of lysine of 0.5-50, or 0.5-40, or 1-30 g/kg.

Crude protein is calculated as nitrogen (N) multiplied by a factor 6.25, i.e. Crude protein (g/kg)=N (g/kg)×6.25 as stated in Animal Nutrition, 4th edition, Chapter 13 (Eds. P. McDonald, R. A. Edwards and J. F. D. Greenhalgh, Longman Scientific and Technical, 1988, ISBN 0-582-40903-9). The nitrogen content can be determined by the Kjeldahl method (A.O.A.C., 1984, Official Methods of Analysis 14th ed., Association of Official Analytical Chemists, Washington D.C.). But also other methods can be used, such as the so-called Dumas method in which the sample is combusted in oxygen and the amount of nitrous gasses formed are analysed and recalculated as nitrogen.

Metabolisable energy can be calculated on the basis of the NRC publication Nutrient Requirements of Swine (1988) pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

In a particular embodiment, the animal feed composition of the invention contains at least one vegetable protein or protein source. Examples of vegetable proteins or protein sources are soybean, peas and rape seed from leguminosae and *brassica* families, and the cereals such as barley, maize (corn), oat, rice, rye, sorghum and wheat.

Animal diets can e.g. be manufactured as mash feed (non-pelleted) or pelleted feed.

Typically, the milled feed-stuffs are mixed and sufficient amounts of essential vitamins and minerals are added according to the specifications for the species in question.

The phytase and protease of the invention can be added in the form of a solid or liquid enzyme formulation, or in the form of a feed additive, such as a pre-mix. A solid composition is typically added before or during the mixing step; and a liquid composition is typically added after the pelleting step.

The phytase and protease of the invention when added to animal feed leads to an improved nutritional value of the feed, e.g. the growth rate and/or the weight gain and/or the feed conversion (i.e. the weight of ingested feed relative to weight gain) of the animal is/are improved.

In particular embodiments the weight gain is at least 101, 102, 103, 104, 105, 106, 107, 108, 109, or at least 110% of the control (no enzyme addition).

In further particular embodiments the feed conversion is at most (or not more than) 99, 98, 97, 96, 95, 94, 93, 92, 91 or at most 90%, as compared to the control (no enzyme addition).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The present invention is further described by the following examples which should not be construed as limiting the scope of the invention.

Example 1: Specific Activity of Phytases

The specific activity of phytases can be determined on highly purified samples dialysed against 20 mM sodium acetate, pH 5.5. The purity can be checked beforehand on an SDS poly acryl amide gel showing the presence of only one component.

The protein concentration can be determined by amino acid analysis as follows: An aliquot of the sample is hydrolyzed in 6N HCl, 0.1% phenol for 16 h at 110 C in an evacuated glass tube. The resulting amino acids are quantified using an Applied Biosystems 420A amino acid analysis system operated according to the manufacturer's instructions. From the amounts of the amino acids the total mass—and thus also the concentration—of protein in the hydrolyzed aliquot can be calculated.

The phytase activity is determined in the units of FYT, and the specific activity is calculated as the phytase activity measured in FYT units per mg phytase variant enzyme protein. Phytase activity can be determined using the assay below.

Determination of Phytase Activity 75 microliter phytase-containing enzyme solution, appropriately diluted in 0.25M sodium acetate, 0.005% (w/v) Tween-20, pH5.5, is dispensed in a microtiter plate well, e. g. NUNC 269620, and 75 microliter substrate is added (prepared by dissolving 100 mg sodium phytate from rice (Aldrich Cat. No. 274321) in 10 ml 0.25M sodium acetate buffer, pH5.5). The plate is sealed and incubated 15 min. shaken with 750 rpm at 37° C. After incubation, 75 microliter stop reagent is added (the stop reagent being prepared by mixing 10 ml molybdate solution (10% (w/v) ammonium hepta-molybdate in 0.25% (w/v) ammonia solution), 10 ml ammonium vanadate (0.24% commercial product from Bie&Berntsen, Cat. No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic orthophosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes A/S, Krogshoejvej 36, DK-2880 Bagsvaerd).

Example 2: In Vivo Broiler Trial 1

The effect on the growth performance of broilers using feed with different amounts and combinations of enzymes (Ronozyme®ProAct & Ronozyme®HiPhos) was investigated. The trial ran 21 days and had 7 treatments with 6 replicate cages of 6 birds per cage.

The diet (NC-Diet) as used in the trial was a diet with low avP/Ca and moderate phytate concentrations (table 1). The experimental conditions are shown in table 2 and the results are presented in table 3.

TABLE 1

Diet

| | Amount |
|---|---|
| Ingredients (%) | |
| Wheat | 59.40 |
| Soybean meal | 23.49 |
| Corn oil | 5.21 |
| Rapeseed solv ext | 5.00 |
| Wheat bran | 4.00 |
| NaCl | 0.15 |
| NaHCO3 | 0.31 |
| DL-methionine | 0.20 |
| Lysine HCl | 0.24 |
| Threonine | 0.06 |
| Limestone | 0.80 |
| Dicalcium phosphate | 0.60 |
| Choline chloride | 0.05 |
| Vitamin Premix | 0.50 |
| Analyzed content | |
| Crude protein (%) | 21.00 |
| Metabolizable energy (MJ/kg) | 3058.8 |
| Ca % | 0.70 |
| P % | 0.57 |
| Available P % | 0.28 |
| Fat | 6.83 |
| Fibre | 3.14 |
| Phytate P % | 0.22 |
| Lysine (%) | 1.20 |
| Cysteine + Methionine (%) | 0.90 |

TABLE 2

Experimental Treatments (T)

| Treatment | Conditions |
|---|---|
| T1 | NC + 15,000 units protease (Ronozyme ®ProAct) |
| T2 | NC + 1,000 FYT phytase (Ronozyme ®HiPhos) |
| T3 | NC + 1,000 FYT phytase + 15,000 units protease |
| T4 | NC + 2,000 FYT phytase (Ronozyme ®HiPhos) |
| T5 | NC + 2,000 FYT phytase + 15,000 units protease |
| T6 | NC + 3,000 FYT phytase |
| T7 | NC + 3,000 FYT phytase + 15,000 units protease |

TABLE 3

Results

| Treatment | Weight Gain (g/bird) | FCR |
|---|---|---|
| T1 | 785 | 1.670 |
| T2 | 905 | 1.451 |
| T3 | 900 | 1.452 |
| T4 | 905 | 1.475 |
| T5 | 912 | 1.461 |
| T6 | 870 | 1.542 |
| T7 | 866 | 1.391 |
| SEM | 30.4318 | 0.0432 |
| Significance (P=) | 1.120 | 0.004 |

In particular the FCR results show that the protease benefits increasingly from higher and higher phytase dosing. With respect to the combination of the enzyme products Ronozyme®ProAct & Ronozyme®HiPhos as exemplified herein above, the really strong protease effect was surprisingly seen at 3000 FYT/kg phytase activity.

Example 3: In Vivo Broiler Trial 2

The effect on the growth performance of broilers using feed with different amounts and combinations of phytase and protease (Ronozyme®ProAct & Axtra®PHY) was investigated. The individual treatments are given in table 4. The trial ran 36 days and each treatment had 6 replicate cages of 18 birds per cage.

The diet (NC-Diet) as used in the trial is a diet with low avP/Ca (see table 5 and table 6).

TABLE 4

Experimental Treatments (T)

| Treatment | Conditions |
|---|---|
| T1 | NC + 500 U/kg Phytase Axtra ®PHY |
| T2 | NC + 500 U/kg Phytase Axtra ®PHY + 15,000 units protease |
| T3 | NC + 1500 U/kg Phytase Axtra ®PHY |
| T4 | NC + 1500 U/kg Phytase Axtra ®PHY + 15,000 units protease |

TABLE 5

Nutrient Composition of Diet

| Diet | Crude protein (%) | ME (MJ/kg) | Lysine (%) | Cysteine + Methionine (%) | P total (%) | P disponible (%) | Ca total (%) |
|---|---|---|---|---|---|---|---|
| Starter | 21.1 | 12.8 | 1.28 | 0.959 | 0.623 | 0.323 | 0.762 |
| Grower | 19.2 | 13.0 | 1.115 | 0.844 | 0.580 | 0.304 | 0.754 |

TABLE 6

Diet

| Ingredients (%) | Starter | Grower |
|---|---|---|
| Wheat, 12.5% CP | 55.50 | 61.00 |
| SBM, 48% CP | 28.00 | 22.36 |
| RSM | 5.00 | 5.00 |
| Wheat bran | 3.82 | 4.00 |
| Soja oil | 4.20 | 4.20 |
| NaCl | 0.20 | 0.20 |
| DL Methionine | 0.26 | 0.20 |
| L-Lysine | 0.24 | 0.22 |
| L-Threonine | 0.12 | 0.11 |
| CaCO$_3$ (%) | 0.40 | 0.50 |
| DCP (%) | 1.25 | 1.05 |
| Premix (%) | 1.00 | 1.00 |
| Lasalocid (Avatec)(%) | 0.06 | 0.06 |
| Titanium dioxide | — | 0.10 |

TABLE 7

Results

| Treatment | Weight Gain (g/bird) | FCR |
|---|---|---|
| T1 | 2690 | 1.54 |
| T2 | 2517 | 1.59 |
| T3 | 2612 | 1.62 |
| T4 | 2549 | 1.54 |

The results show that the phytase in combination with protease benefits from higher phytase dosing. The combination of the commercial dose of Axtra®PHY together with Ronozyme®ProAct did not result in any performance improvement over the commercial dose of Axtra®PHY alone. However, the combination of 3 times the amount of the commercial dose of Axtra®PHY together with Ronozyme®ProAct surprisingly resulted in a strong FCR improvement over 3 times the amount of the commercial dose of Axtra®PHY alone.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for improving Feed Conversion Ratio of a farm animal, comprising applying to the animal a feed comprising at least one protease and at least one phytase wherein:
   a. the phytase is administered in an amount that the specific activity in the feed is 3000 FYT/kg feed and
   b. the protease is administered at a dosage of between 10000 units/kg feed and 30000 units/kg feed.

2. The method of claim 1, the protease is administered at a dosage selected from the group consisting of 10000, 11000, 12000, 13000, 14000, 15000, 16000, 17000, 18000, 19000, and 20000 units/kg feed.

3. The method of claim 1, wherein the protease is administered at a dosage of 15000 units/kg feed.

4. The method of claim 1, wherein the phytase is classified as belonging to the EC 3.1.3.26 group.

5. The method of claim 1, wherein the phytase is derived from the family Enterobacteriaceae.

6. The method of claim 1, wherein the protease is an acid stable serine protease obtained or obtainable from the class Actinobacteria.

7. The method of claim 1, wherein the protease comprises the amino acid sequence of any of SEQ ID NOs: 27-48.

8. The method of claim 1, wherein the farm animal is selected from the group consisting of pigs, swine, poultry, turkeys, ducks, quail, guinea fowl, geese, pigeons and chicken.

9. A method for improving Feed Conversion Ratio of a farm animal, comprising applying to the animal a feed comprising at least one protease and at least one phytase wherein:
   a. the phytase is administered in an amount that the specific activity in the feed is 3000 FYT/kg feed and
   b. the protease is administered at a dosage of 15000 units/kg feed.

10. The method of claim 9, wherein the phytase is classified as belonging to the EC 3.1.3.26 group.

11. The method of claim 9, wherein the phytase is derived from the family Enterobacteriaceae.

12. The method of claim 9, wherein the protease is an acid stable serine protease obtained or obtainable from the class Actinobacteria.

13. The method of claim 9, wherein the protease comprises the amino acid sequence of any of SEQ ID NOs: 27-48.

14. The method of claim 9, wherein the farm animal is selected from the group consisting of pigs, swine, poultry, turkeys, ducks, quail, guinea fowl, geese, pigeons and chicken.

* * * * *

SEQUENCE LISTING

```
<160> NUMBER OF SEQ ID NOS: 48

<210> SEQ ID NO 1
<211> LENGTH: 410
<212> TYPE: PRT
<213> ORGANISM: E.Coli

<400> SEQUENCE: 1

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285
```

```
Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 2
<211> LENGTH: 410
<212> TYPE: PRT
<213> ORGANISM: E.Coli

<400> SEQUENCE: 2

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Ser Gln Leu Asn
                165                 170                 175

Leu Cys Leu Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255
```

```
Leu Gln Arg Thr Pro Glu Val Ala Arg Ser Arg Ala Thr Pro Leu Leu
            260                 265                 270

Asp Leu Ile Met Ala Ala Leu Thr Pro His Pro Gln Lys Gln Ala
            275                 280                 285

Tyr Gly Val Thr Leu Pro Thr Ser Val Leu Phe Ile Ala Gly His Asp
290                 295                 300

Thr Asn Leu Ala Asn Leu Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 3
<211> LENGTH: 410
<212> TYPE: PRT
<213> ORGANISM: Artificial Sequence
<220> FEATURE:
<223> OTHER INFORMATION: E. Coli variant

<400> SEQUENCE: 3

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Cys Val Ser Leu Thr
        195                 200                 205
```

```
Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 4
<211> LENGTH: 410
<212> TYPE: PRT
<213> ORGANISM: Artificial Sequence
<220> FEATURE:
<223> OTHER INFORMATION: E. Coli variant

<400> SEQUENCE: 4

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
    115                 120                 125

Lys Thr Gly Val Cys Gln Leu Asp Val Ala Asn Val Arg Arg Ala Ile
130                 135                 140

Leu Glu Arg Ala Gly Gly Ser Ile Ala Asp Phe Thr Arg His Tyr Gln
145                 150                 155                 160
```

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asp Val Ser Leu Thr
        195                 200                 205

Gly Ala Trp Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Val Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 5
<211> LENGTH: 418
<212> TYPE: PRT
<213> ORGANISM: Artificial Sequence
<220> FEATURE:
<223> OTHER INFORMATION: E. Coli variant

<400> SEQUENCE: 5

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu Arg Ser His His His
                405                 410                 415

His His

<210> SEQ ID NO 6
<211> LENGTH: 410
<212> TYPE: PRT
<213> ORGANISM: Artificial Sequence
<220> FEATURE:
<223> OTHER INFORMATION: E. Coli variant

<400> SEQUENCE: 6

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

-continued

```
Pro Arg Gly Gly Glu Leu Ile Ala Tyr Leu Gly His Tyr Gln Arg Gln
     50                  55                  60

Arg Leu Val Ala Asp Gly Leu Leu Ala Lys Lys Gly Cys Pro Gln Pro
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 7
<211> LENGTH: 411
<212> TYPE: PRT
<213> ORGANISM: Artificial Sequence
<220> FEATURE:
<223> OTHER INFORMATION: E. Coli variant

<400> SEQUENCE: 7
```

-continued

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Glu Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asp Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```

```
<210> SEQ ID NO 8
<211> LENGTH: 411
<212> TYPE: PRT
<213> ORGANISM: Artificial Sequence
<220> FEATURE:
<223> OTHER INFORMATION: E. Coli variant

<400> SEQUENCE: 8

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Val Ala Asn Val Thr Arg Ala
    130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asp Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
```

```
              370                 375                 380
Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 9
<211> LENGTH: 411
<212> TYPE: PRT
<213> ORGANISM: Artificial Sequence
<220> FEATURE:
<223> OTHER INFORMATION: E. Coli variant

<400> SEQUENCE: 9

Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala His Leu Gly His Tyr Trp Arg
        50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Tyr Pro Pro Gly Gly Glu Leu Val Phe
```

```
                     325                 330                 335
Glu Arg Trp Arg Arg Leu Ser Asp Asn Ser Gln Trp Ile Gln Val Ser
                340                 345                 350
Leu Val Phe Gln Thr Leu Gln Gln Met Arg Asp Lys Thr Pro Leu Ser
            355                 360                 365
Leu Asn Thr Pro Pro Gly Glu Val Lys Leu Thr Leu Ala Gly Cys Glu
        370                 375                 380
Glu Arg Asn Ala Gln Gly Met Cys Ser Leu Ala Gly Phe Thr Gln Ile
385                 390                 395                 400
Val Asn Glu Ala Arg Ile Pro Ala Cys Ser Leu
                405                 410

<210> SEQ ID NO 10
<211> LENGTH: 411
<212> TYPE: PRT
<213> ORGANISM: Citrobacter braakii ATCC 51113

<400> SEQUENCE: 10

Glu Glu Gln Asn Gly Met Lys Leu Glu Arg Val Val Ile Val Ser Arg
1               5                   10                  15
His Gly Val Arg Ala Pro Thr Lys Phe Thr Pro Ile Met Lys Asn Val
            20                  25                  30
Thr Pro Asp Gln Trp Pro Gln Trp Asp Val Pro Leu Gly Trp Leu Thr
        35                  40                  45
Pro Arg Gly Gly Glu Leu Val Ser Glu Leu Gly Gln Tyr Gln Arg Leu
    50                  55                  60
Trp Phe Thr Ser Lys Gly Leu Leu Asn Asn Gln Thr Cys Pro Ser Pro
65                  70                  75                  80
Gly Gln Val Ala Val Ile Ala Asp Thr Asp Gln Arg Thr Arg Lys Thr
                85                  90                  95
Gly Glu Ala Phe Leu Ala Gly Leu Ala Pro Lys Cys Gln Ile Gln Val
            100                 105                 110
His Tyr Gln Lys Asp Glu Glu Lys Asn Asp Pro Leu Phe Asn Pro Val
        115                 120                 125
Lys Met Gly Lys Cys Ser Phe Asn Thr Leu Gln Val Lys Asn Ala Ile
    130                 135                 140
Leu Glu Arg Ala Gly Gly Asn Ile Glu Leu Tyr Thr Gln Arg Tyr Gln
145                 150                 155                 160
Ser Ser Phe Arg Thr Leu Glu Asn Val Leu Asn Phe Ser Gln Ser Glu
                165                 170                 175
Thr Cys Lys Thr Thr Glu Lys Ser Thr Lys Cys Thr Leu Pro Glu Ala
            180                 185                 190
Leu Pro Ser Glu Leu Lys Val Thr Pro Asp Asn Val Ser Leu Pro Gly
        195                 200                 205
Ala Trp Ser Leu Ser Ser Thr Leu Thr Glu Ile Phe Leu Leu Gln Glu
    210                 215                 220
Ala Gln Gly Met Pro Gln Val Ala Trp Gly Arg Ile Thr Gly Glu Lys
225                 230                 235                 240
Glu Trp Arg Asp Leu Leu Ser Leu His Asn Ala Gln Phe Asp Leu Leu
                245                 250                 255
Gln Arg Thr Pro Glu Val Ala Arg Ser Arg Ala Thr Pro Leu Leu Asp
            260                 265                 270
Met Ile Asp Thr Ala Leu Leu Thr Asn Gly Thr Thr Glu Asn Arg Tyr
        275                 280                 285
```

```
Gly Ile Lys Leu Pro Val Ser Leu Leu Phe Ile Ala Gly His Asp Thr
        290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
                340                 345                 350

Tyr Gln Thr Leu Arg Asp Met Arg Asp Ile Gln Pro Leu Ser Leu Glu
                355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 11
<211> LENGTH: 410
<212> TYPE: PRT
<213> ORGANISM: Citrobacter gillenii

<400> SEQUENCE: 11

Asp Glu Gln Ser Gly Met Gln Leu Glu Arg Val Val Ile Val Ser Arg
1               5                   10                  15

His Gly Val Arg Ala Pro Thr Lys Phe Thr Pro Leu Met Gln Gln Val
                20                  25                  30

Thr Pro Asp Arg Trp Pro Gln Trp Asp Val Pro Leu Gly Trp Leu Thr
            35                  40                  45

Pro Arg Gly Gly Ala Leu Ile Thr Glu Leu Gly Arg Tyr Gln Arg Leu
        50                  55                  60

Arg Leu Ala Asp Lys Gly Leu Leu Asp Asn Lys Thr Cys Pro Thr Ala
65                  70                  75                  80

Gly Gln Val Ala Val Ile Ala Asp Ser Asp Gln Arg Thr Arg Lys Thr
                85                  90                  95

Gly Glu Ala Phe Leu Ala Gly Leu Ala Pro Glu Cys Lys Val Gln Val
            100                 105                 110

Tyr Tyr Gln Gln Asp Lys Ser Lys Ser Asp Pro Leu Phe Asn Pro Ile
        115                 120                 125

Lys Ala Gly Arg Cys Ser Leu Asn Thr Ser Gln Val Lys Glu Ala Ile
130                 135                 140

Leu Thr Arg Ala Gly Gly Ser Leu Asp Glu Tyr Thr Arg His Tyr Gln
145                 150                 155                 160

Pro Ala Phe Gln Ala Leu Glu Arg Val Leu Asn Phe Ser Gln Ser Glu
                165                 170                 175

Lys Cys Gln Ala Ala Gly Gln Ser Ala Gln Cys Thr Leu Thr Asp Val
            180                 185                 190

Leu Pro Ala Glu Leu Lys Val Ser Pro Glu Asn Ile Ser Leu Ser Gly
        195                 200                 205

Ser Trp Gly Leu Ala Ser Thr Leu Thr Glu Ile Phe Leu Leu Gln Gln
210                 215                 220

Ala Gln Gly Met Ser Gln Val Ala Trp Gly Arg Ile His Gly Asp Lys
225                 230                 235                 240

Glu Trp Arg Thr Leu Leu Ser Leu His Asn Ala Gln Phe Asp Leu Leu
                245                 250                 255
```

```
Gln Lys Thr Pro Glu Val Ala Arg Ser Arg Ala Thr Pro Leu Leu Asp
                260                 265                 270

Leu Ile Arg Thr Ala Leu Val Thr Gln Gly Ala Thr Glu Asn Lys Tyr
            275                 280                 285

Ala Ile Gln Leu Pro Val Ser Leu Leu Phe Ile Ala Gly His Asp Thr
        290                 295                 300

Asn Leu Ala Asn Ile Ser Gly Ala Leu Gly Leu Asn Val Phe Leu Pro
305                 310                 315                 320

Gly Gln Pro Asp Asn Thr Pro Pro Gly Gly Glu Phe Val Phe Glu Arg
                325                 330                 335

Trp Lys Arg Val Ser Asp His Ser Asp Trp Val Gln Val Ser Phe Met
            340                 345                 350

Tyr Gln Thr Leu Gln Glu Met Arg Asp Met Gln Pro Leu Ser Leu Gln
        355                 360                 365

Ser Pro Pro Gly Lys Ile Val Leu Pro Leu Ala Ala Cys Asp Glu Lys
    370                 375                 380

Asn Thr Gln Gly Met Cys Ser Leu Lys Asn Phe Ser Ala Leu Ile Asp
385                 390                 395                 400

Ser Val Arg Val Ser Glu Cys Ala Glu Lys
                405                 410

<210> SEQ ID NO 12
<211> LENGTH: 414
<212> TYPE: PRT
<213> ORGANISM: Citrobacter amalonaticus

<400> SEQUENCE: 12

Glu Val Pro Asp Asp Met Lys Leu Glu Arg Val Val Ile Val Ser Arg
1               5                   10                  15

His Gly Val Arg Ala Pro Thr Lys Phe Thr Pro Leu Met Gln Glu Ile
                20                  25                  30

Thr Pro Tyr His Trp Pro Gln Trp Asp Val Pro Leu Gly Trp Leu Thr
            35                  40                  45

Ala Arg Gly Gly Glu Leu Val Thr Glu Met Gly Arg Tyr Gln Gln Lys
        50                  55                  60

Val Leu Ile Asp Asn Gly Val Leu Glu Ser Asn Val Cys Pro Ser Pro
65                  70                  75                  80

Glu Gln Val Ala Val Ile Ala Asp Thr Asp Gln Arg Thr Arg Lys Thr
                85                  90                  95

Gly Glu Ala Phe Leu Ala Gly Phe Ala Pro Gly Cys Lys Asn Lys Val
            100                 105                 110

His Tyr Gln Lys Asp His Asp Lys Lys Asp Pro Leu Phe Asn Pro Val
        115                 120                 125

Lys Met Gly Val Cys Ala Phe Asn Val Gln Lys Thr Gln Glu Ala Ile
    130                 135                 140

Leu Thr Arg Ala Glu Gly Asn Ile Glu Arg Tyr Thr Gln Arg Tyr Asp
145                 150                 155                 160

Ser Ala Phe Arg Thr Leu Glu Gln Val Leu Asn Phe Ser Arg Ser Ala
                165                 170                 175

Ala Cys Arg Ser Ala Ser Gln Ser Gly Cys Thr Leu Pro Gly Thr Leu
            180                 185                 190

Pro Ser Glu Leu Arg Val Ser Ala Asp Thr Val Ser Leu Ser Gly Ala
        195                 200                 205

Trp Ser Leu Ser Ser Met Leu Thr Glu Ile Phe Leu Leu Gln Glu Ala
```

-continued

```
            210                 215                 220
Gln Gly Met Pro Glu Val Ala Trp Gly Arg Ile His Gly Lys Glu
225                 230                 235                 240

Trp Thr Ala Leu Leu Ser Leu His Asn Ala Gln Phe Asp Leu Leu Gln
                    245                 250                 255

Arg Thr Pro Glu Val Ala Arg Ser Arg Ala Thr Pro Leu Leu Asp Leu
                260                 265                 270

Ile Ser Glu Ala Leu Val Ser Asn Gly Ser Thr Glu Asn His Tyr Gly
                275                 280                 285

Ile Lys Leu Pro Val Ser Leu Leu Phe Ile Ala Gly His Asp Thr Asn
                290                 295                 300

Leu Ala Asn Leu Ser Gly Val Phe Asp Leu Asn Trp Ser Leu Pro Gly
305                 310                 315                 320

Gln Pro Asp Asn Thr Pro Pro Gly Gly Glu Leu Val Phe Glu Arg Trp
                    325                 330                 335

Thr Arg Val Ser Asp Asn Thr Asp Trp Ile Gln Ile Ser Phe Val Tyr
                340                 345                 350

Gln Thr Leu Gln Gln Met Arg Lys Phe Lys Pro Phe Ser Ser Ser Ser
                355                 360                 365

Leu Pro Asn Lys Ile Val Leu Thr Leu Pro Ser Cys Gln Asp Lys Asn
370                 375                 380

Pro Glu Gly Met Cys Pro Leu Lys His Phe Ile Asp Ile Val Gln Thr
385                 390                 395                 400

Ala Arg Ile Pro Gln Cys Ala Val Met Ala Asp Val Asn Arg
                    405                 410

<210> SEQ ID NO 13
<211> LENGTH: 411
<212> TYPE: PRT
<213> ORGANISM: Citrobacter braakii YH-15 KCCM 10427

<400> SEQUENCE: 13

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
                20                  25                  30

Thr Pro Asp Gln Trp Pro Gln Trp Asp Val Pro Leu Gly Trp Leu Thr
            35                  40                  45

Pro Arg Gly Gly Glu Leu Val Ser Glu Leu Gly Gln Tyr Gln Arg Leu
        50                  55                  60

Trp Phe Thr Ser Lys Gly Leu Leu Asn Asn Gln Thr Cys Pro Ser Pro
65              70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
            115                 120                 125

Lys Met Gly Lys Cys Ser Phe Asn Thr Leu Lys Val Lys Asn Ala Ile
        130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175
```

```
Thr Cys Lys Thr Thr Glu Lys Ser Thr Lys Cys Thr Leu Pro Glu Ala
            180                 185                 190

Leu Pro Ser Glu Phe Lys Val Thr Pro Asp Asn Val Ser Leu Pro Gly
            195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
            275                 280                 285

Gly Ile Lys Leu Pro Val Ser Leu Leu Phe Ile Ala Gly His Asp Thr
            290                 295                 300

Asn Leu Ala Asn Leu Ser Gly Ala Leu Asp Leu Lys Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
            355                 360                 365

Lys Pro Ala Gly Lys Val Asp Leu Lys Leu Ile Ala Cys Glu Glu Lys
            370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 14
<211> LENGTH: 411
<212> TYPE: PRT
<213> ORGANISM: Citrobacter freundii P3-42

<400> SEQUENCE: 14

Glu Glu Pro Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Thr Asp Pro Leu Phe Asn Pro Val
        115                 120                 125

Lys Met Gly Thr Cys Ser Phe Asn Thr Leu Lys Val Lys Asn Ala Ile
    130                 135                 140
```

```
Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
                195                 200                 205

Ala Trp Ser Leu Ser Ser Thr Leu Thr Glu Ile Phe Leu Leu Gln Glu
        210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
                260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
        290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
                340                 345                 350

Tyr Gln Thr Leu Arg Asp Met Arg Asp Ile Gln Pro Leu Ser Leu Glu
                355                 360                 365

Lys Pro Ala Gly Lys Val Asp Leu Lys Leu Ile Ala Cys Glu Glu Lys
                370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 15
<211> LENGTH: 413
<212> TYPE: PRT
<213> ORGANISM: Buttiauxella sp P1-29

<400> SEQUENCE: 15

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Glu Cys His Leu
```

```
            100                 105                 110
Thr Ile His His Gln Gln Asp Ile Lys Lys Ala Asp Pro Leu Phe His
            115                 120                 125

Pro Val Lys Ala Gly Thr Cys Ser Met Asp Lys Thr Gln Val Gln Gln
            130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
            195                 200                 205

Ala Leu Asp Gly Ala Ile Gly Leu Ser Ser Thr Leu Ala Glu Ile Phe
            210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
            290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
            370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 16
<211> LENGTH: 413
<212> TYPE: PRT
<213> ORGANISM: Buttiauxella sp. P1-29

<400> SEQUENCE: 16

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60
```

```
Arg Gln Lys Phe Gln Gln Gly Ile Leu Ser Gln Gly Ser Cys Pro
 65                  70                  75                  80

Thr Pro Asn Ser Ile Tyr Val Trp Ala Asp Val Asp Gln Arg Thr Leu
                 85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 17
<211> LENGTH: 413
<212> TYPE: PRT
<213> ORGANISM: Artificial Sequence
<220> FEATURE:
<223> OTHER INFORMATION: Buttiauxella variant

<400> SEQUENCE: 17

Asn Asp Thr Pro Ala Ser Gly Tyr Gln Val Glu Lys Val Val Ile Leu
 1               5                  10                  15
```

-continued

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
 50                  55                  60

Arg Gln Lys Phe Gln Gln Gly Ile Leu Ser Gln Gly Ser Cys Pro
 65              70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
            195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 18
<211> LENGTH: 413
<212> TYPE: PRT

<213> ORGANISM: Buttiauxella gaviniae DSM18930

<400> SEQUENCE: 18

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Arg Leu Gln Gln
    130                 135                 140

Ala Val Glu Lys Glu Ala Gln Thr Pro Ile Glu Asn Leu Asn Gln His
145                 150                 155                 160

Tyr Ile Pro Ser Leu Ala Leu Met Asn Thr Thr Leu Asn Phe Ser Thr
                165                 170                 175

Ser Ala Trp Cys Gln Lys His Ser Ala Asp Lys Ser Cys Asp Leu Ala
            180                 185                 190

Gln Ser Met Pro Ser Lys Leu Ser Ile Lys Asp Asn Gly Asn Lys Val
        195                 200                 205

Ala Leu Asp Gly Ala Val Gly Leu Ser Ser Thr Leu Ala Glu Ile Phe
    210                 215                 220

Leu Leu Glu Tyr Ala Gln Gly Met Pro Gln Ala Ala Trp Gly Lys Ile
225                 230                 235                 240

His Ser Glu Gln Asp Trp Ala Glu Leu Leu Lys Leu His Asn Ala Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asp Pro Asn Ala Thr Ala
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ser Gly Met Leu Asn Met Arg
305                 310                 315                 320

Trp Thr Leu Pro Gly Gln Pro Asp Asn Thr Pro Pro Gly Gly Ala Leu
                325                 330                 335

Ile Phe Glu Arg Leu Ala Asp Lys Ala Gly Lys Gln Tyr Val Ser Val
            340                 345                 350

Ser Met Val Tyr Gln Thr Leu Glu Gln Leu Arg Ala Gln Thr Pro Leu
        355                 360                 365

Ser Leu Lys Glu Pro Ala Gly Ser Val Gln Leu Lys Ile Pro Gly Cys
    370                 375                 380

Asn Asp Gln Thr Ala Glu Gly Tyr Cys Pro Leu Pro Thr Phe Lys Arg
385                 390                 395                 400
```

-continued

Val Val Ser Gln Ser Glu Glu Pro Gly Cys Gln Leu Gln
            405                 410

<210> SEQ ID NO 19
<211> LENGTH: 413
<212> TYPE: PRT
<213> ORGANISM: Buttiauxella agrestis DSM18931

<400> SEQUENCE: 19

Ser Asp Thr Pro Ala Ser Gly Tyr Gln Ile Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Ser Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Lys Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Met Pro Ile Glu Asn Leu Asn Gln His
145                 150                 155                 160

Tyr Ile Pro Ser Leu Ala Leu Met Asn Thr Thr Leu Asn Phe Ser Thr
                165                 170                 175

Ser Ala Trp Cys Gln Lys His Ser Ala Asp Lys Ser Cys Asp Leu Ala
            180                 185                 190

Gln Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Thr Gln
                245                 250                 255

Phe Asp Leu Met Ala Arg Thr Pro Tyr Ile Ala Ala His Asn Gly Thr
            260                 265                 270

Pro Leu Leu Gln Thr Ile Ser Asn Ala Leu Glu Pro Lys Ala Asp Val
        275                 280                 285

Ser Lys Leu Pro Asp Ile Ser Ser Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Ile Ser Val
            340                 345                 350

Ser Met Val Tyr Gln Thr Leu Glu Gln Leu Arg Ala Gln Thr Pro Leu
        355                 360                 365

-continued

Ser Leu Asn Glu Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Pro
                405                 410

<210> SEQ ID NO 20
<211> LENGTH: 413
<212> TYPE: PRT
<213> ORGANISM: Buttiauxella agrestis DSM18932

<400> SEQUENCE: 20

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Glu Lys Phe Gln Gln Gly Ile Leu Ser Gln Gly Ser Cys Pro
65                  70                  75                  80

Ala Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Thr
                165                 170                 175

Ser Ala Trp Cys Gln Lys His Ser Ala Asp Lys Ser Cys Asp Leu Ala
            180                 185                 190

Gln Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Ala Gln
                245                 250                 255

Phe Asp Leu Met Ala Arg Thr Pro Tyr Ile Ala Thr His Asn Gly Thr
            260                 265                 270

Pro Leu Leu Gln Thr Ile Ser Asn Ala Leu Glu Pro Lys Ala Asp Val
        275                 280                 285

Ser Lys Leu Pro Gly Ile Ser Pro Asp Asn Lys Ile Leu Phe Leu Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu

```
                        325                 330                 335
Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
        370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 21
<211> LENGTH: 410
<212> TYPE: PRT
<213> ORGANISM: Peniophora lycii CBS No. 686.96

<400> SEQUENCE: 21

Gln Leu Pro Ile Pro Ala Gln Asn Thr Ser Asn Trp Gly Pro Tyr Asp
1               5                   10                  15

Pro Phe Phe Pro Val Glu Pro Tyr Ala Ala Pro Pro Glu Gly Cys Thr
            20                  25                  30

Val Thr Gln Val Asn Leu Ile Gln Arg His Gly Ala Arg Trp Pro Thr
        35                  40                  45

Ser Gly Ala Arg Ser Arg Gln Val Ala Val Ala Lys Ile Gln Met
    50                  55                  60

Ala Arg Pro Phe Thr Asp Pro Lys Tyr Glu Phe Leu Asn Asp Phe Val
65                  70                  75                  80

Tyr Lys Phe Gly Val Ala Asp Leu Leu Pro Phe Gly Ala Asn Gln Ser
                85                  90                  95

His Gln Thr Gly Thr Asp Met Tyr Thr Arg Tyr Ser Thr Leu Phe Glu
            100                 105                 110

Gly Gly Asp Val Pro Phe Val Arg Ala Ala Gly Asp Gln Arg Val Val
        115                 120                 125

Asp Ser Ser Thr Asn Trp Thr Ala Gly Phe Gly Asp Ala Ser Gly Glu
    130                 135                 140

Thr Val Leu Pro Thr Leu Gln Val Val Leu Gln Glu Glu Gly Asn Cys
145                 150                 155                 160

Thr Leu Cys Asn Asn Met Cys Pro Asn Glu Val Asp Gly Asp Glu Ser
                165                 170                 175

Thr Thr Trp Leu Gly Val Phe Ala Pro Asn Ile Thr Ala Arg Leu Asn
            180                 185                 190

Ala Ala Ala Pro Ser Ala Asn Leu Ser Asp Ser Asp Ala Leu Thr Leu
        195                 200                 205

Met Asp Met Cys Pro Phe Asp Thr Leu Ser Ser Gly Asn Ala Ser Pro
    210                 215                 220

Phe Cys Asp Leu Phe Thr Ala Glu Glu Tyr Val Ser Tyr Glu Tyr
225                 230                 235                 240

Tyr Asp Leu Asp Lys Tyr Tyr Gly Thr Gly Pro Gly Asn Ala Leu Gly
                245                 250                 255

Pro Val Gln Gly Val Gly Tyr Val Asn Glu Leu Leu Ala Arg Leu Thr
            260                 265                 270

Gly Gln Ala Val Arg Asp Glu Thr Gln Thr Asn Arg Thr Leu Asp Ser
        275                 280                 285
```

```
Asp Pro Ala Thr Phe Pro Leu Asn Arg Thr Phe Tyr Ala Asp Phe Ser
    290                 295                 300

His Asp Asn Thr Met Val Pro Ile Phe Ala Ala Leu Gly Leu Phe Asn
305                 310                 315                 320

Ala Thr Ala Leu Asp Pro Leu Lys Pro Asp Glu Asn Arg Leu Trp Val
                325                 330                 335

Asp Ser Lys Leu Val Pro Phe Ser Gly His Met Thr Val Glu Lys Leu
            340                 345                 350

Ala Cys Ser Gly Lys Glu Ala Arg Val Leu Val Asn Asp Ala Val
        355                 360                 365

Gln Pro Leu Glu Phe Cys Gly Val Asp Gly Val Cys Glu Leu Ser
370                 375                 380

Ala Phe Val Glu Ser Gln Thr Tyr Ala Arg Glu Asn Gly Gln Gly Asp
385                 390                 395                 400

Phe Ala Lys Cys Gly Phe Val Pro Ser Glu
                405                 410

<210> SEQ ID NO 22
<211> LENGTH: 410
<212> TYPE: PRT
<213> ORGANISM: Artificial Sequence
<220> FEATURE:
<223> OTHER INFORMATION: Peniophora variant

<400> SEQUENCE: 22

Gln Leu Pro Ile Pro Ala Gln Asn Thr Ser Asn Trp Gly Pro Tyr Ser
1               5                   10                  15

Pro Phe Phe Pro Val Glu Pro Tyr Ala Ala Pro Glu Gly Cys Thr
                20                  25                  30

Val Thr Gln Val Asn Leu Ile Gln Arg His Gly Ala Arg Trp Pro Thr
            35                  40                  45

Ser Gly Ala Arg Ser Arg Gln Val Ala Ala Val Ala Lys Ile Gln Met
    50                  55                  60

Ala Arg Pro Phe Thr Asp Pro Lys Tyr Glu Phe Leu Asn Asp Phe Val
65                  70                  75                  80

Tyr Thr Phe Gly Val Ala Asp Leu Leu Pro Phe Gly Ala Asn Gln Ser
                85                  90                  95

Tyr Gln Thr Gly Thr Asp Met Tyr Thr Arg Tyr Ser Thr Leu Phe Glu
                100                 105                 110

Gly Gly Asp Val Pro Phe Val Arg Ala Ala Gly Asp Gln Arg Val Val
            115                 120                 125

Asp Ser Ser Thr Asn Trp Thr Ala Gly Phe Gly Asp Ala Ser Gly Glu
    130                 135                 140

Thr Val Leu Pro Thr Leu Gln Val Val Leu Gln Glu Glu Gly Asn Cys
145                 150                 155                 160

Thr Leu Cys Asn Asn Met Cys Pro Asn Trp Val Lys Gly Asp Glu Ser
                165                 170                 175

Thr Thr Trp Leu Gly Val Phe Ala Pro Asn Ile Thr Ala Arg Leu Asn
                180                 185                 190

Ala Ala Ala Pro Ser Ala Asn Leu Ser Asp Ser Asp Ala Leu Thr Leu
            195                 200                 205

Met Asp Met Cys Pro Phe Asp Thr Leu Ser Ser Gly Asn Ala Ser Pro
    210                 215                 220

Phe Cys Asp Leu Phe Thr Ala Glu Glu Tyr Thr Ser Tyr Glu Tyr Tyr
225                 230                 235                 240
```

Tyr Asp Leu Asp Lys Tyr Tyr Gly Thr Gly Pro Gly Asn Ala Leu Gly
            245                 250                 255

Pro Val Gln Gly Val Gly Tyr Val Asn Glu Leu Leu Ala Arg Leu Thr
        260                 265                 270

Gly Gln Ala Val Arg Asp Glu Thr Gln Thr Asn Arg Thr Leu Asp Ser
    275                 280                 285

Asp Pro Ala Thr Phe Pro Leu Asn Arg Thr Phe Tyr Ala Asp Phe Ser
290                 295                 300

His Asp Asn Thr Met Val Ala Ile Phe Ala Ala Leu Gly Leu Phe Asn
305                 310                 315                 320

Ala Thr Ala Leu Asp Pro Leu Lys Pro Asp Glu Asn Arg Leu Trp Val
                325                 330                 335

Val Ser Lys Leu Val Pro Phe Ser Gly His Met Thr Val Glu Lys Leu
            340                 345                 350

Ala Cys Ser Gly Lys Glu Ala Val Arg Val Leu Val Asn Asp Ala Val
        355                 360                 365

Gln Pro Leu Glu Phe Cys Gly Val Asp Gly Val Cys Glu Leu Ser
    370                 375                 380

Ala Phe Val Glu Ser Gln Thr Tyr Ala Arg Glu Asn Gly Gln Gly Asp
385                 390                 395                 400

Phe Ala Lys Cys Gly Phe Val Pro Ser Glu
                405                 410

<210> SEQ ID NO 23
<211> LENGTH: 413
<212> TYPE: PRT
<213> ORGANISM: Hafnia alvei

<400> SEQUENCE: 23

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Thr Gln Gln Ala Asp Pro Leu Phe His
        115                 120                 125

Pro Val Lys Ala Gly Ile Cys Ser Met Asp Lys Ser Gln Val His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

```
Ala Leu Glu Gly Ala Val Gly Leu Ala Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asn Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Thr Ser
        275                 280                 285

Arg Pro Leu Pro Asp Ile Ser Pro Asp Asn Lys Ile Leu Phe Ile Ala
290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Ala Leu
                325                 330                 335

Val Phe Glu Arg Trp Val Asp Asn Ala Gly Lys Pro Tyr Val Ser Val
            340                 345                 350

Asn Met Val Tyr Gln Thr Leu Ala Gln Leu His Asp Gln Ala Pro Leu
        355                 360                 365

Thr Leu Gln His Pro Ala Gly Ser Val Arg Leu Asn Ile Pro Gly Cys
    370                 375                 380

Ser Asp Gln Thr Pro Asp Gly Tyr Cys Pro Leu Ser Thr Phe Ser Arg
385                 390                 395                 400

Leu Val Ser His Ser Val Glu Pro Ala Cys Gln Leu Pro
                405                 410

<210> SEQ ID NO 24
<211> LENGTH: 413
<212> TYPE: PRT
<213> ORGANISM: Hafnia sp. LU11047

<400> SEQUENCE: 24

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asn Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
```

```
            165                 170                 175
Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
            195                 200             205

Ala Leu Glu Gly Ala Val Gly Leu Ser Ser Thr Leu Ala Glu Ile Phe
        210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Ala Ser
                275                 280                 285

Arg Pro Leu Pro Asp Ile Ser Pro Asp Asn Lys Ile Leu Phe Ile Ala
        290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Gly Gly Ala Leu
                325                 330                 335

Val Phe Glu Arg Trp Val Asp Asn Ala Gly Lys Pro Tyr Val Ser Val
            340                 345                 350

Asn Met Val Tyr Gln Thr Leu Ala Gln Leu His Asp Gln Thr Pro Leu
                355                 360                 365

Thr Leu Gln His Pro Ala Gly Ser Val Arg Leu Asn Ile Pro Gly Cys
        370                 375                 380

Ser Asp Gln Thr Pro Asp Gly Tyr Cys Pro Leu Ser Thr Phe Ser Arg
385                 390                 395                 400

Leu Val Asn His Ser Val Glu Pro Ala Cys Gln Leu Pro
                405                 410

<210> SEQ ID NO 25
<211> LENGTH: 414
<212> TYPE: PRT
<213> ORGANISM: Artificial Sequence
<220> FEATURE:
<223> OTHER INFORMATION: Hafnia variant

<400> SEQUENCE: 25

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asn Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
```

```
                    115                 120                 125
    Pro Val Lys Ala Gly Ile Cys Ser Met Asp Lys Ser Gln Ala His Ala
                130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                    165                 170                 175

Ser Pro Tyr Cys Gln Gln His Asn Ile Gly Lys Leu Cys Asp Phe Ser
                180                 185                 190

Gln Ala Met Pro Ser Arg Leu Ala Ile Asn Asp Asp Gly Asn Lys Val
                195                 200                 205

Ala Leu Glu Gly Ala Val Gly Leu Ser Ser Thr Leu Ala Glu Ile Phe
                210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                    245                 250                 255

Phe Asp Leu Met Ser Arg Thr Pro Tyr Ile Ala Lys His Asn Gly Thr
                260                 265                 270

Pro Leu Leu Gln Thr Ile Ala His Ala Leu Gly Ser Asn Ile Ala Ser
                275                 280                 285

Arg Pro Leu Pro Asp Ile Ser Pro Asp Asn Lys Ile Leu Phe Ile Ala
290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Gly Gly Gly Leu
                    325                 330                 335

Val Phe Glu Leu Trp Gln Asn Pro Asp Asn His Gln Gln Tyr Val Ala
                340                 345                 350

Val Lys Met Phe Tyr Gln Thr Met Asp Gln Leu Arg Asn Ser Glu Lys
                355                 360                 365

Leu Asp Leu Lys Ser His Pro Ala Gly Ile Val Pro Ile Glu Ile Glu
                370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys His Ile
                    405                 410

<210> SEQ ID NO 26
<211> LENGTH: 414
<212> TYPE: PRT
<213> ORGANISM: Artificial Sequence
<220> FEATURE:
<223> OTHER INFORMATION: Hafnia variant

<400> SEQUENCE: 26

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Glu Arg Phe Gln Gln Gln Gly Leu Leu Pro Lys Asp Asn Cys Pro
```

65                  70                  75                  80
Thr Pro Asp Ala Val Tyr Val Trp Thr Asp Val Asn Gln Arg Thr Arg
                    85                  90                  95

Lys Thr Gly Glu Ala Phe Leu Ala Gly Leu Ala Pro Gln Cys Asp Leu
                100                 105                 110

Ala Ile His His Gln Gln Asn Ile Thr Gln Val Asp Pro Leu Phe His
            115                 120                 125

Pro Val Lys Ala Gly Ile Cys Ser Met Asn Lys Ser Gln Thr Tyr Glu
130                 135                 140

Ala Val Glu Lys Gln Ala Gly Gly Pro Ile Glu Thr Leu Asn Gln Arg
145                 150                 155                 160

Tyr Gln Ala Glu Leu Ala Leu Met Ser Ser Val Leu Asp Phe Pro Lys
                    165                 170                 175

Ser Pro Tyr Cys Gln Gln His Asn Ile Gly Lys Leu Cys Asp Phe Ser
                180                 185                 190

Gln Ala Met Pro Ser Arg Leu Asn Ile Ser Asp Asp Gly Asn Glu Val
            195                 200                 205

Gln Leu Glu Gly Ala Val Gly Leu Gly Ser Thr Leu Ala Glu Ile Phe
        210                 215                 220

Leu Leu Glu Tyr Ala Gln Gly Met Pro Val Val Ala Trp Gly Asn Ile
225                 230                 235                 240

His Asn Glu Ser Gln Trp Lys Ser Leu Leu Asn Leu His Asn Ala His
                    245                 250                 255

Phe Asn Leu Met His Arg Thr Pro Tyr Ile Ala Lys His Gln Gly Thr
                260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Gly Gly Met Leu Gly Met Asn
305                 310                 315                 320

Trp Thr Leu Pro Gly Gln Pro Asp Asn Thr Pro Gly Gly Leu
                    325                 330                 335

Val Phe Glu Leu Trp Gln Asn Pro Asp Asn His Gln Gln Tyr Val Ala
                340                 345                 350

Val Lys Met Ile Tyr Gln Thr Met Asp Gln Leu Arg Asn Ser Glu Lys
            355                 360                 365

Leu Asp Leu Lys Ser Asn Pro Ala Gly Ile Val Pro Ile Glu Ile Glu
        370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys Gln Ile
                    405                 410

<210> SEQ ID NO 27
<211> LENGTH: 354
<212> TYPE: PRT
<213> ORGANISM: Nocardiopsis dassonvillei subsp. dassonvillei DSM 43235

<400> SEQUENCE: 27

Ala Pro Ala Pro Val Pro Gln Thr Pro Val Ala Asp Asp Ser Ala Ala
1               5                   10                  15

Ser Met Thr Glu Ala Leu Lys Arg Asp Leu Asp Leu Thr Ser Ala Glu
                20                  25                  30

```
Ala Glu Glu Leu Leu Ser Ala Gln Glu Ala Ala Ile Glu Thr Asp Ala
            35                  40                  45

Glu Ala Thr Glu Ala Ala Gly Glu Ala Tyr Gly Gly Ser Leu Phe Asp
 50                  55                  60

Thr Glu Thr Leu Glu Leu Thr Val Leu Val Thr Asp Ala Ser Ala Val
 65                  70                  75                  80

Glu Ala Val Glu Ala Thr Gly Ala Gln Ala Thr Val Val Ser His Gly
                85                  90                  95

Thr Glu Gly Leu Thr Glu Val Val Glu Asp Leu Asn Gly Ala Glu Val
            100                 105                 110

Pro Glu Ser Val Leu Gly Trp Tyr Pro Asp Val Glu Ser Asp Thr Val
            115                 120                 125

Val Val Glu Val Leu Glu Gly Ser Asp Ala Asp Val Ala Ala Leu Leu
130                 135                 140

Ala Asp Ala Gly Val Asp Ser Ser Val Arg Val Glu Glu Ala Glu
145                 150                 155                 160

Glu Ala Pro Gln Val Tyr Ala Asp Ile Ile Gly Gly Leu Ala Tyr Tyr
                165                 170                 175

Met Gly Gly Arg Cys Ser Val Gly Phe Ala Ala Thr Asn Ser Ala Gly
            180                 185                 190

Gln Pro Gly Phe Val Thr Ala Gly His Cys Gly Thr Val Gly Thr Gly
            195                 200                 205

Val Thr Ile Gly Asn Gly Thr Gly Thr Phe Gln Asn Ser Val Phe Pro
            210                 215                 220

Gly Asn Asp Ala Ala Phe Val Arg Gly Thr Ser Asn Phe Thr Leu Thr
225                 230                 235                 240

Asn Leu Val Ser Arg Tyr Asn Ser Gly Gly Tyr Gln Ser Val Thr Gly
                245                 250                 255

Thr Ser Gln Ala Pro Ala Gly Ser Ala Val Cys Arg Ser Gly Ser Thr
            260                 265                 270

Thr Gly Trp His Cys Gly Thr Ile Gln Ala Arg Asn Gln Thr Val Arg
            275                 280                 285

Tyr Pro Gln Gly Thr Val Tyr Ser Leu Thr Arg Thr Asn Val Cys Ala
290                 295                 300

Glu Pro Gly Asp Ser Gly Gly Ser Phe Ile Ser Gly Ser Gln Ala Gln
305                 310                 315                 320

Gly Val Thr Ser Gly Gly Ser Gly Asn Cys Ser Val Gly Gly Thr Thr
                325                 330                 335

Tyr Tyr Gln Glu Val Thr Pro Met Ile Asn Ser Trp Gly Val Arg Ile
            340                 345                 350

Arg Thr

<210> SEQ ID NO 28
<211> LENGTH: 269
<212> TYPE: PRT
<213> ORGANISM: Bacillus clausii

<400> SEQUENCE: 28

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45
```

```
Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
                210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

<210> SEQ ID NO 29
<211> LENGTH: 384
<212> TYPE: PRT
<213> ORGANISM: Nocardiopsis sp. DSM 16424

<400> SEQUENCE: 29

Met Arg Pro Ser Thr Ile Ala Ser Ala Val Gly Thr Gly Ala Leu Ala
 1               5                  10                  15

Phe Gly Leu Ala Leu Ser Met Ala Pro Gly Ala Leu Ala Ala Pro Gly
                 20                  25                  30

Pro Val Pro Gln Thr Pro Val Ala Asp Asp Ser Ala Ala Ser Met Thr
                 35                  40                  45

Glu Ala Leu Lys Arg Asp Leu Asn Leu Ser Ser Ala Glu Ala Glu Glu
 50                  55                  60

Leu Leu Ser Ala Gln Glu Ala Ala Ile Glu Thr Asp Ala Glu Ala Ala
 65                  70                  75                  80

Glu Ala Ala Gly Glu Ala Tyr Gly Gly Ser Leu Phe Asp Thr Glu Thr
                 85                  90                  95

Leu Glu Leu Thr Val Leu Val Thr Asp Thr Thr Ala Val Asp Ala Val
                100                 105                 110

Glu Ala Thr Gly Ala Glu Ala Thr Val Val Thr His Gly Thr Asp Gly
                115                 120                 125

Leu Ala Glu Val Val Glu Asp Leu Asn Ser Ala Asp Ala Pro Ala Gly
130                 135                 140

Val Leu Gly Trp Tyr Pro Asp Met Glu Ser Asp Thr Val Val Val Glu
145                 150                 155                 160
```

Val Leu Glu Gly Ser Asp Ala Asp Val Ala Ala Leu Ala Asp Ala
            165                 170                 175

Gly Val Asp Ala Ser Ala Val Arg Val Glu Ala Glu Glu Val Pro
            180                 185                 190

Gln Val Tyr Ala Asn Ile Ile Gly Gly Leu Ala Tyr Thr Met Gly Gly
            195                 200                 205

Arg Cys Ser Val Gly Phe Ala Ala Thr Asn Ser Ala Gly Gln Pro Gly
            210                 215                 220

Phe Val Thr Ala Gly His Cys Gly Thr Val Gly Thr Ala Val Thr Ile
225                 230                 235                 240

Gly Asp Gly Arg Gly Val Phe Glu Arg Ser Val Phe Pro Gly Asn Asp
            245                 250                 255

Ala Ala Phe Val Arg Gly Thr Ser Asn Phe Thr Leu Thr Asn Leu Val
            260                 265                 270

Ser Arg Tyr Asn Ser Gly Gly His Gln Ala Val Thr Gly Thr Ser Gln
            275                 280                 285

Ala Pro Ala Gly Ser Ala Val Cys Arg Ser Gly Ser Thr Thr Gly Trp
            290                 295                 300

His Cys Gly Thr Ile Gln Ala Arg Asn Gln Thr Val Arg Tyr Pro Gln
305                 310                 315                 320

Gly Thr Val Asn Ala Leu Thr Arg Thr Asn Val Cys Ala Glu Pro Gly
            325                 330                 335

Asp Ser Gly Gly Ser Phe Ile Ser Gly Ser Gln Ala Gln Gly Val Thr
            340                 345                 350

Ser Gly Gly Ser Gly Asn Cys Ser Phe Gly Gly Thr Thr Tyr Tyr Gln
            355                 360                 365

Glu Val Ala Pro Met Ile Asn Ser Trp Gly Val Arg Ile Arg Thr Ser
            370                 375                 380

<210> SEQ ID NO 30
<211> LENGTH: 355
<212> TYPE: PRT
<213> ORGANISM: Nocardiopsis alba DSM 15647

<400> SEQUENCE: 30

Ala Thr Gly Pro Leu Pro Gln Ser Pro Thr Pro Asp Glu Ala Glu Ala
1               5                   10                  15

Thr Thr Met Val Glu Ala Leu Gln Arg Asp Leu Gly Leu Ser Pro Ser
                20                  25                  30

Gln Ala Asp Glu Leu Leu Glu Ala Gln Ala Glu Ser Phe Glu Ile Asp
            35                  40                  45

Glu Ala Ala Thr Ala Ala Ala Ala Asp Ser Tyr Gly Gly Ser Ile Phe
        50                  55                  60

Asp Thr Asp Ser Leu Thr Leu Thr Val Leu Val Thr Asp Ala Ser Ala
65                  70                  75                  80

Val Glu Ala Val Glu Ala Gly Ala Glu Ala Lys Val Val Ser His
                85                  90                  95

Gly Met Glu Gly Leu Glu Glu Ile Val Ala Asp Leu Asn Ala Ala Asp
                100                 105                 110

Ala Gln Pro Gly Val Val Gly Trp Tyr Pro Asp Ile His Ser Asp Thr
            115                 120                 125

Val Val Leu Glu Val Leu Glu Gly Ser Gly Ala Asp Val Asp Ser Leu
        130                 135                 140

Leu Ala Asp Ala Gly Val Asp Thr Ala Asp Val Lys Val Glu Ser Thr

```
                145                 150                 155                 160
        Thr Glu Gln Pro Glu Leu Tyr Ala Asp Ile Ile Gly Gly Leu Ala Tyr
                        165                 170                 175
        Thr Met Gly Gly Arg Cys Ser Val Gly Phe Ala Ala Thr Asn Ala Ser
                        180                 185                 190
        Gly Gln Pro Gly Phe Val Thr Ala Gly His Cys Gly Thr Val Gly Thr
                        195                 200                 205
        Pro Val Ser Ile Gly Asn Gly Gln Gly Val Phe Glu Arg Ser Val Phe
                        210                 215                 220
        Pro Gly Asn Asp Ser Ala Phe Val Arg Gly Thr Ser Asn Phe Thr Leu
        225                 230                 235                 240
        Thr Asn Leu Val Ser Arg Tyr Asn Thr Gly Gly Tyr Ala Thr Val Ser
                        245                 250                 255
        Gly Ser Ser Gln Ala Ala Ile Gly Ser Gln Ile Cys Arg Ser Gly Ser
                        260                 265                 270
        Thr Thr Gly Trp His Cys Gly Thr Val Gln Ala Arg Gly Gln Thr Val
                        275                 280                 285
        Ser Tyr Pro Gln Gly Thr Val Gln Asn Leu Thr Arg Thr Asn Val Cys
                        290                 295                 300
        Ala Glu Pro Gly Asp Ser Gly Gly Ser Phe Ile Ser Gly Ser Gln Ala
        305                 310                 315                 320
        Gln Gly Val Thr Ser Gly Gly Ser Gly Asn Cys Ser Phe Gly Gly Thr
                        325                 330                 335
        Thr Tyr Tyr Gln Glu Val Asn Pro Met Leu Ser Ser Trp Gly Leu Thr
                        340                 345                 350
        Leu Arg Thr
                355

<210> SEQ ID NO 31
<211> LENGTH: 381
<212> TYPE: PRT
<213> ORGANISM: Nocardiopsis dassonvillei subsp. dassonvillei DSM 43235

<400> SEQUENCE: 31

Met Arg Pro Ser Pro Ala Ile Ser Ala Ile Gly Thr Gly Ala Leu Ala
        1               5                   10                  15
        Phe Gly Leu Ala Phe Ser Val Thr Pro Gly Ala Ser Ala Ala Thr Val
                        20                  25                  30
        Pro Ala Glu Pro Ala Ser Glu Ala Gln Thr Met Met Glu Ala Leu Gln
                        35                  40                  45
        Arg Asp Leu Gly Leu Thr Pro Leu Gly Ala Glu Leu Leu Ser Ala
        50                  55                  60
        Gln Glu Glu Ala Ile Glu Thr Asp Ala Glu Ala Thr Glu Ala Ala Gly
        65                  70                  75                  80
        Ala Ser Tyr Gly Gly Ser Leu Phe Asp Thr Glu Thr Leu Gln Leu Thr
                        85                  90                  95
        Val Leu Val Thr Asp Ala Ser Ala Val Glu Ala Val Glu Ala Thr Gly
                        100                 105                 110
        Ala Glu Ala Thr Val Val Ser His Gly Ala Glu Gly Leu Ala Glu Val
                        115                 120                 125
        Val Asp Ala Leu Asp Glu Thr Gly Gly Arg Glu Gly Val Val Gly Trp
                        130                 135                 140
        Tyr Pro Asp Val Glu Ser Asp Thr Val Val Val Gln Val Ala Glu Gly
        145                 150                 155                 160
```

```
Ala Ser Ala Asp Gly Leu Ile Glu Ala Ala Gly Val Asp Pro Ser Ala
            165                 170                 175

Val Arg Val Glu Glu Thr Ser Glu Thr Pro Arg Leu Tyr Ala Asp Ile
        180                 185                 190

Val Gly Gly Glu Ala Tyr Tyr Met Gly Gly Arg Cys Ser Val Gly
        195                 200                 205

Phe Ala Val Thr Asp Gly Ser Gly Ala Gly Gly Phe Val Thr Ala Gly
        210                 215                 220

His Cys Gly Thr Val Gly Thr Gly Ala Glu Ser Ser Asp Gly Ser Gly
225                 230                 235                 240

Ser Gly Thr Phe Gln Glu Ser Val Phe Pro Gly Ser Asp Gly Ala Phe
            245                 250                 255

Val Ala Ala Thr Ser Asn Trp Asn Val Thr Asn Leu Val Ser Arg Tyr
            260                 265                 270

Asp Ser Gly Ser Pro Gln Ala Val Ser Gly Ser Ser Gln Ala Pro Glu
        275                 280                 285

Gly Ser Ala Val Cys Arg Ser Gly Ser Thr Thr Gly Trp His Cys Gly
        290                 295                 300

Thr Ile Glu Ala Arg Gly Gln Thr Val Asn Tyr Pro Gln Gly Thr Val
305                 310                 315                 320

Gln Asp Leu Thr Arg Thr Asp Val Cys Ala Glu Pro Gly Asp Ser Gly
            325                 330                 335

Gly Ser Phe Ile Ala Gly Ser Gln Ala Gln Gly Val Thr Ser Gly Gly
            340                 345                 350

Ser Gly Asn Cys Thr Ser Gly Gly Thr Thr Tyr Tyr Gln Glu Val Thr
            355                 360                 365

Pro Leu Leu Ser Ser Trp Gly Leu Ser Leu Val Thr Gly
        370                 375                 380

<210> SEQ ID NO 32
<211> LENGTH: 188
<212> TYPE: PRT
<213> ORGANISM: Nocardiopsis sp. NRRL 18262

<400> SEQUENCE: 32

Ala Asp Ile Ile Gly Gly Leu Ala Tyr Thr Met Gly Gly Arg Cys Ser
1               5                  10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160
```

Ser Gly Asn Cys Arg Thr Gly Thr Thr Phe Tyr Gln Glu Val Thr
        165                 170                 175

Pro Met Val Asn Ser Trp Gly Val Arg Leu Arg Thr
        180                 185

<210> SEQ ID NO 33
<211> LENGTH: 353
<212> TYPE: PRT
<213> ORGANISM: Nocardiopsis prasina DSM 15648

<400> SEQUENCE: 33

Ala Thr Gly Pro Leu Pro Gln Ser Pro Thr Pro Glu Ala Asp Ala Val
1               5                   10                  15

Ser Met Gln Glu Ala Leu Gln Arg Asp Leu Gly Leu Thr Pro Leu Glu
            20                  25                  30

Ala Asp Glu Leu Leu Ala Ala Gln Asp Thr Ala Phe Glu Val Asp Glu
        35                  40                  45

Ala Ala Ala Ala Ala Gly Asp Ala Tyr Gly Gly Ser Val Phe Asp
        50                  55                  60

Thr Glu Thr Leu Glu Leu Thr Val Leu Val Thr Asp Ala Ala Ser Val
65                  70                  75                  80

Glu Ala Val Glu Ala Thr Gly Ala Gly Thr Glu Leu Val Ser Tyr Gly
                85                  90                  95

Ile Glu Gly Leu Asp Glu Ile Ile Gln Asp Leu Asn Ala Ala Asp Ala
            100                 105                 110

Val Pro Gly Val Gly Trp Tyr Pro Asp Val Ala Gly Asp Thr Val
        115                 120                 125

Val Leu Glu Val Leu Glu Gly Ser Gly Ala Asp Val Ser Gly Leu Leu
        130                 135                 140

Ala Asp Ala Gly Val Asp Ala Ser Ala Val Glu Val Thr Ser Ser Ala
145                 150                 155                 160

Gln Pro Glu Leu Tyr Ala Asp Ile Ile Gly Gly Leu Ala Tyr Thr Met
                165                 170                 175

Gly Gly Arg Cys Ser Val Gly Phe Ala Ala Thr Asn Ala Ala Gly Gln
            180                 185                 190

Pro Gly Phe Val Thr Ala Gly His Cys Gly Arg Val Gly Thr Gln Val
        195                 200                 205

Ser Ile Gly Asn Gly Gln Gly Val Phe Glu Gln Ser Ile Phe Pro Gly
    210                 215                 220

Asn Asp Ala Ala Phe Val Arg Gly Thr Ser Asn Phe Thr Leu Thr Asn
225                 230                 235                 240

Leu Val Ser Arg Tyr Asn Thr Gly Gly Tyr Ala Thr Val Ala Gly His
                245                 250                 255

Asn Gln Ala Pro Ile Gly Ser Ser Val Cys Arg Ser Gly Ser Thr Thr
            260                 265                 270

Gly Trp His Cys Gly Thr Ile Gln Ala Arg Gly Gln Ser Val Ser Tyr
        275                 280                 285

Pro Glu Gly Thr Val Thr Asn Met Thr Arg Thr Thr Val Cys Ala Glu
    290                 295                 300

Pro Gly Asp Ser Gly Gly Ser Tyr Ile Ser Gly Asn Gln Ala Gln Gly
305                 310                 315                 320

Val Thr Ser Gly Gly Ser Gly Asn Cys Arg Thr Gly Gly Thr Thr Phe
                325                 330                 335

Tyr Gln Glu Val Thr Pro Met Val Asn Ser Trp Gly Val Arg Leu Arg

Thr

<210> SEQ ID NO 34
<211> LENGTH: 353
<212> TYPE: PRT
<213> ORGANISM: Nocardiopsis prasina DSM 15649

<400> SEQUENCE: 34

Ala Thr Gly Pro Leu Pro Gln Ser Pro Thr Pro Glu Ala Asp Ala Val
1               5                   10                  15

Ser Met Gln Glu Ala Leu Gln Arg Asp Leu Gly Leu Thr Pro Leu Glu
            20                  25                  30

Ala Asp Glu Leu Leu Ala Ala Gln Asp Thr Ala Phe Glu Val Asp Glu
        35                  40                  45

Ala Ala Ala Glu Ala Ala Gly Asp Ala Tyr Gly Gly Ser Val Phe Asp
    50                  55                  60

Thr Glu Thr Leu Glu Leu Thr Val Leu Val Thr Asp Ser Ala Ala Val
65                  70                  75                  80

Glu Ala Val Glu Ala Thr Gly Ala Gly Thr Glu Leu Val Ser Tyr Gly
                85                  90                  95

Ile Thr Gly Leu Asp Glu Ile Val Glu Glu Leu Asn Ala Ala Asp Ala
            100                 105                 110

Val Pro Gly Val Val Gly Trp Tyr Pro Asp Val Ala Gly Asp Thr Val
        115                 120                 125

Val Leu Glu Val Leu Glu Gly Ser Gly Ala Asp Val Gly Gly Leu Leu
    130                 135                 140

Ala Asp Ala Gly Val Asp Ala Ser Ala Val Glu Val Thr Thr Thr Glu
145                 150                 155                 160

Gln Pro Glu Leu Tyr Ala Asp Ile Ile Gly Gly Leu Ala Tyr Thr Met
                165                 170                 175

Gly Gly Arg Cys Ser Val Gly Phe Ala Ala Thr Asn Ala Ala Gly Gln
            180                 185                 190

Pro Gly Phe Val Thr Ala Gly His Cys Gly Arg Val Gly Thr Gln Val
        195                 200                 205

Thr Ile Gly Asn Gly Arg Gly Val Phe Glu Gln Ser Ile Phe Pro Gly
    210                 215                 220

Asn Asp Ala Ala Phe Val Arg Gly Thr Ser Asn Phe Thr Leu Thr Asn
225                 230                 235                 240

Leu Val Ser Arg Tyr Asn Thr Gly Gly Tyr Ala Thr Val Ala Gly His
                245                 250                 255

Asn Gln Ala Pro Ile Gly Ser Ser Val Cys Arg Ser Gly Ser Thr Thr
            260                 265                 270

Gly Trp His Cys Gly Thr Ile Gln Ala Arg Gly Gln Ser Val Ser Tyr
        275                 280                 285

Pro Glu Gly Thr Val Thr Asn Met Thr Arg Thr Val Cys Ala Glu
    290                 295                 300

Pro Gly Asp Ser Gly Gly Ser Tyr Ile Ser Gly Asn Gln Ala Gln Gly
305                 310                 315                 320

Val Thr Ser Gly Gly Ser Gly Asn Cys Arg Thr Gly Thr Thr Phe
                325                 330                 335

Tyr Gln Glu Val Thr Pro Met Val Asn Ser Trp Gly Val Arg Leu Arg
            340                 345                 350

Thr

<210> SEQ ID NO 35
<211> LENGTH: 383
<212> TYPE: PRT
<213> ORGANISM: Nocardiopsis prasina DSM 15649

<400> SEQUENCE: 35

Met Arg Pro Ser Pro Val Ile Ser Ala Ile Gly Thr Gly Ala Leu Ala
1               5                   10                  15

Phe Gly Leu Ala Leu Ser Val Ala Pro Gly Ala Ser Ala Val Thr Ala
            20                  25                  30

Pro Thr Glu Pro Ala Pro Gln Gly Glu Ala Ala Thr Met Gln Glu Ala
        35                  40                  45

Leu Glu Arg Asp Phe Gly Leu Thr Pro Phe Glu Ala Glu Asp Leu Leu
    50                  55                  60

Glu Ala Gln Asn Asp Ala Leu Gly Ile Asp Thr Ala Ala Ala Lys Ala
65                  70                  75                  80

Ala Gly Asp Ala Tyr Ala Gly Ser Val Phe Asp Thr Asp Thr Leu Glu
                85                  90                  95

Leu Thr Val Leu Leu Thr Asp Ala Gly Ala Val Ser Asp Val Glu Ala
            100                 105                 110

Thr Gly Ala Gly Thr Glu Leu Val Ser Tyr Gly Thr Glu Gly Leu Ala
        115                 120                 125

Glu Ile Met Asp Glu Leu Asp Ala Ala Gly Ala Gln Pro Gly Val Val
    130                 135                 140

Gly Trp Tyr Pro Asp Leu Ala Gly Asp Thr Val Val Ile Glu Ala Thr
145                 150                 155                 160

Asp Thr Ser Glu Ala Gln Ser Phe Val Glu Ala Gly Val Asp Ser
                165                 170                 175

Ser Ala Val Gln Val Glu Gln Thr Asp Glu Ala Pro Gln Leu Tyr Ala
            180                 185                 190

Asp Ile Val Gly Gly Asp Ala Tyr Tyr Met Gly Gly Arg Cys Ser
        195                 200                 205

Val Gly Phe Ala Val Thr Asp Ser Ser Gly Asn Asp Gly Phe Val Thr
    210                 215                 220

Ala Gly His Cys Gly Thr Val Gly Thr Ser Ala Asp Ser Glu Asp Gly
225                 230                 235                 240

Ser Gly Ser Gly Val Phe Glu Glu Ser Ile Phe Pro Gly Asn Asp Ala
                245                 250                 255

Ala Phe Val Ser Ser Thr Ser Asn Trp Thr Val Thr Asn Leu Val Asn
            260                 265                 270

Met Tyr Ser Ser Gly Thr Gln Ser Val Gly Gly Ser Ser Gln Ala
        275                 280                 285

Pro Val Gly Ala Ala Val Cys Arg Ser Gly Ser Thr Thr Gly Trp His
    290                 295                 300

Cys Gly Ser Ile Glu Ala Arg Gly Gln Ser Val Ser Tyr Pro Glu Gly
305                 310                 315                 320

Thr Val Thr Asp Met Thr Arg Thr Asp Val Cys Ala Glu Pro Gly Asp
                325                 330                 335

Ser Gly Gly Ser Phe Ile Ala Asp Asp Gln Ala Gln Met Thr Ser
            340                 345                 350

Gly Gly Ser Gly Asn Cys Ser Ser Gly Gly Thr Thr Tyr Tyr Gln Glu
        355                 360                 365

Val Gly Pro Ala Leu Ser Thr Trp Asn Leu Ser Leu Val Thr Ser

<210> SEQ ID NO 36
<211> LENGTH: 383
<212> TYPE: PRT
<213> ORGANISM: Nocardiopsis prasina DSM 14010

<400> SEQUENCE: 36

Met Arg Pro Ser Pro Val Ile Ser Ala Ile Gly Thr Gly Ala Leu Ala
1               5                   10                  15

Phe Gly Leu Ala Leu Ser Val Ala Pro Gly Ala Ser Ala Val Thr Ala
                20                  25                  30

Pro Ala Glu Pro Ser Pro Gln Gly Glu Ala Thr Thr Met Gln Glu Ala
            35                  40                  45

Leu Glu Arg Asp Phe Gly Leu Thr Pro Phe Glu Ala Asp Asp Leu Leu
    50                  55                  60

Glu Ala Gln Lys Glu Ala Leu Gly Ile Asp Thr Ala Ala Ala Glu Ala
65                  70                  75                  80

Ala Gly Asp Ala Tyr Ala Gly Ser Val Phe Asp Thr Asp Thr Leu Glu
                85                  90                  95

Leu Thr Val Leu Leu Thr Asp Gly Gly Pro Ala Ser Asp Val Glu Ala
            100                 105                 110

Ala Gly Ala Glu Thr Ser Val Val Ser His Gly Thr Asp Gly Leu Ala
        115                 120                 125

Ala Ile Met Asp Glu Leu Asp Ala Val Gly Ala Gln Pro Gly Val Val
130                 135                 140

Gly Trp Tyr Pro Asp Leu Ala Ser Asp Thr Val Val Glu Ala Thr
145                 150                 155                 160

Asp Ala Ser Asp Ala Gln Gly Phe Ile Glu Ala Ala Gly Val Asp Ser
                165                 170                 175

Ser Ala Val Gln Val Glu Glu Thr Asp Glu Ser Pro Glu Leu Tyr Ala
            180                 185                 190

Asp Ile Val Gly Gly Asp Ala Tyr Tyr Met Gly Gly Gly Arg Cys Ser
        195                 200                 205

Val Gly Phe Ala Ala Thr Asp Ser Ala Gly Asn Asp Gly Phe Val Thr
210                 215                 220

Ala Gly His Cys Gly Thr Val Gly Thr Ser Ala Asp Ser Glu Asp Gly
225                 230                 235                 240

Ser Gly Ser Gly Val Phe Glu Glu Ser Ile Phe Pro Gly Asn Asp Ala
                245                 250                 255

Ala Phe Val Arg Ser Thr Ser Asn Trp Thr Val Thr Asn Leu Val Asn
            260                 265                 270

Met Tyr Ser Ser Gly Thr Gln Ser Val Gly Gly Ser Thr Gln Ala
        275                 280                 285

Pro Val Gly Ala Ala Val Cys Arg Ser Gly Ser Thr Thr Gly Trp His
    290                 295                 300

Cys Gly Thr Ile Glu Ala Arg Gly Gln Ser Val Ser Tyr Pro Glu Gly
305                 310                 315                 320

Thr Val Asn Asp Met Thr Arg Thr Asn Val Cys Ala Glu Pro Gly Asp
                325                 330                 335

Ser Gly Gly Ser Phe Ile Ser Asp Asp Gln Ala Gln Gly Met Thr Ser
            340                 345                 350

Gly Gly Ser Gly Asn Cys Thr Ser Gly Gly Thr Thr Tyr Tyr Gln Glu
        355                 360                 365

```
Val Gly Pro Ala Leu Ser Thr Trp Asn Leu Ser Leu Val Thr Ser
    370                 375                 380
```

```
<210> SEQ ID NO 37
<211> LENGTH: 383
<212> TYPE: PRT
<213> ORGANISM: Nocardiopsis alkaliphila DSM 44657

<400> SEQUENCE: 37
```

```
Met Arg Pro Ser Pro Val Val Ser Ala Ile Gly Thr Gly Ala Leu Ala
1               5                   10                  15

Phe Gly Leu Ala Leu Gly Thr Ser Pro Ala Ala Ile Ala Ala Pro Ala
            20                  25                  30

Pro Gln Ser Pro Asp Thr Glu Thr Gln Ala Glu Ala Val Thr Met Ala
        35                  40                  45

Glu Ala Leu Gln Arg Asp Leu Gly Leu Ser Ser Glu Ala Thr Glu
    50                  55                  60

Leu Leu Ala Ala Gln Ala Glu Ala Phe Glu Val Asp Glu Ala Ala Thr
65                  70                  75                  80

Glu Ala Ala Ala Asp Ala Tyr Gly Gly Ser Leu Phe Asp Thr Asp Ser
                85                  90                  95

Leu Glu Leu Thr Val Leu Val Thr Asp Ser Ala Ala Val Asp Ala Val
            100                 105                 110

Glu Ala Thr Gly Ala Lys Ala Glu Val Val Asp His Gly Ile Glu Gly
        115                 120                 125

Leu Glu Glu Ile Val Asp Glu Leu Asn Glu Ser Asn Ala Lys Ser Gly
    130                 135                 140

Val Val Gly Trp Tyr Pro Asp Val Ala Gly Asp Thr Val Val Leu Glu
145                 150                 155                 160

Val Met Glu Gly Ser Glu Ala Asp Val Asp Ala Leu Leu Ala Glu Thr
                165                 170                 175

Gly Val Asp Ala Ala Asp Val Thr Val Glu Thr Thr Glu Gln Pro
            180                 185                 190

Glu Leu Tyr Ala Asp Ile Ile Gly Gly Leu Ala Tyr Thr Met Gly Gly
    195                 200                 205

Arg Cys Ser Val Gly Phe Ala Ala Thr Asn Ser Ser Gly Gln Pro Gly
    210                 215                 220

Phe Val Thr Ala Gly His Cys Gly Ser Val Gly Thr Gly Val Thr Ile
225                 230                 235                 240

Gly Asn Gly Arg Gly Val Phe Glu Arg Ser Ile Phe Pro Gly Asn Asp
                245                 250                 255

Ala Ala Phe Val Arg Gly Thr Ser Asn Phe Thr Leu Thr Asn Leu Val
            260                 265                 270

Ser Arg Tyr Asn Ser Gly Gly Tyr Ala Thr Val Ser Gly Ser Ser Ala
        275                 280                 285

Ala Pro Ile Gly Ser Gln Val Cys Arg Ser Gly Ser Thr Thr Gly Trp
    290                 295                 300

His Cys Gly Thr Ile Gln Ala Arg Asn Gln Thr Val Arg Tyr Pro Gln
305                 310                 315                 320

Gly Thr Val Gln Ala Leu Thr Arg Thr Ser Val Cys Ala Glu Pro Gly
                325                 330                 335

Asp Ser Gly Gly Ser Phe Ile Ser Gly Ser Gln Ala Gln Gly Val Thr
            340                 345                 350

Ser Gly Gly Ser Gly Asn Cys Arg Thr Gly Gly Thr Thr Tyr Tyr Gln
        355                 360                 365
```

Glu Val Asn Pro Met Leu Asn Ser Trp Gly Leu Arg Leu Arg Thr
370                 375                 380

<210> SEQ ID NO 38
<211> LENGTH: 384
<212> TYPE: PRT
<213> ORGANISM: Nocardiopsis lucentensis DSM 44048

<400> SEQUENCE: 38

Met Arg Pro Ser Pro Val Ile Ser Ala Leu Gly Thr Gly Ala Leu Ala
1               5                   10                  15

Phe Gly Leu Val Ile Thr Met Ala Pro Gly Val Asn Ala Gly Thr Val
                20                  25                  30

Pro Thr Pro Gln Ala Pro Val Pro Asp Asp Glu Ala Thr Thr Met Leu
            35                  40                  45

Glu Ala Met Glu Arg Asp Leu Asp Leu Thr Pro Phe Glu Ala Glu Glu
        50                  55                  60

Leu Phe Glu Ala Gln Glu Glu Ala Ile Asp Leu Asp Glu Glu Ala Thr
65                  70                  75                  80

Glu Ala Ala Gly Ala Ala Tyr Gly Gly Ser Leu Phe Asp Thr Glu Thr
                85                  90                  95

His Glu Leu Thr Val Leu Val Thr Asp Val Asp Ala Val Glu Ala Val
                100                 105                 110

Glu Ala Thr Gly Ala Ala Ala Glu Val Val Ser His Gly Ser Asp Gly
            115                 120                 125

Leu Ala Asp Ile Val Glu Asp Leu Asn Ala Thr Asp Ala Gly Ser Glu
130                 135                 140

Val Val Gly Trp Tyr Pro Asp Val Thr Ser Asp Ser Val Val Val Glu
145                 150                 155                 160

Val Val Glu Gly Ser Asp Val Asp Val Asp Ser Ile Val Glu Gly Thr
                165                 170                 175

Gly Val Asp Pro Ala Val Ile Glu Val Gln Glu Val Ser Glu Gln Pro
            180                 185                 190

Gln Thr Tyr Ala Asn Ile Ile Gly Gly Leu Ala Tyr Tyr Met Ser Ser
        195                 200                 205

Gly Gly Arg Cys Ser Val Gly Phe Pro Ala Thr Asn Ser Ser Gly Gln
210                 215                 220

Pro Gly Phe Val Thr Ala Gly His Cys Gly Thr Val Gly Thr Gly Val
225                 230                 235                 240

Thr Ile Gly Asn Gly Arg Gly Thr Phe Glu Arg Ser Val Phe Pro Gly
                245                 250                 255

Asn Asp Ala Ala Phe Val Arg Gly Thr Ser Asn Phe Thr Leu Tyr Asn
            260                 265                 270

Leu Val Tyr Arg Tyr Ser Gly Tyr Gln Thr Val Thr Gly Ser Asn Ala
        275                 280                 285

Ala Pro Ile Gly Ser Ser Ile Cys Arg Ser Gly Ser Thr Thr Gly Trp
290                 295                 300

His Cys Gly Thr Ile Gln Ala Arg Asn Gln Thr Val Arg Tyr Pro Gln
305                 310                 315                 320

Gly Thr Val Tyr Tyr Leu Thr Arg Thr Asn Val Cys Ala Glu Pro Gly
                325                 330                 335

Asp Ser Gly Gly Ser Phe Ile Ser Gly Thr Gln Ala Gln Gly Met Thr
            340                 345                 350

Ser Gly Gly Ser Gly Asn Cys Ser Ser Gly Gly Thr Thr Phe Tyr Gln

```
               355                 360                 365
Glu Val Asp Pro Val Glu Ser Ala Trp Gly Val Arg Leu Arg Thr Ser
    370                 375                 380

<210> SEQ ID NO 39
<211> LENGTH: 188
<212> TYPE: PRT
<213> ORGANISM: Kribella solani

<400> SEQUENCE: 39

Ile Ala Gly Gly Asp Ala Ile Tyr Gly Gly Gln Tyr Arg Cys Ser Leu
1               5                  10                  15

Gly Phe Asn Val Arg Ser Gly Ser Thr Tyr Tyr Phe Leu Thr Ala Gly
            20                  25                  30

His Cys Gly Asn Ile Ala Ser Ser Trp Tyr Ala Asn Ser Ala Lys Thr
        35                  40                  45

Thr Leu Leu Gly Thr Thr Tyr Gly Ser Ser Phe Pro Gly Asn Asp Tyr
    50                  55                  60

Ala Ile Val Gln Tyr Ser Ser Tyr Thr Asn His Pro Gly Thr Val
65                  70                  75                  80

Asp Leu Tyr Asn Gly Ser Ser Gln Asp Ile Thr Ser Ala Gly Asn Ala
                85                  90                  95

Thr Val Gly Gln Ala Val Lys Arg Ser Gly Ser Thr Thr Gly Val His
            100                 105                 110

Ser Gly Ser Val Thr Gly Leu Asn Ala Thr Val Asn Tyr Ala Glu Gly
        115                 120                 125

Thr Val Thr Gly Leu Ile Arg Thr Asn Val Cys Ala Glu Gly Gly Asp
    130                 135                 140

Ser Gly Gly Ala Leu Phe Ala Gly Thr Val Ala Leu Gly Leu Thr Ser
145                 150                 155                 160

Gly Gly Ser Gly Asn Cys Ser Ser Gly Gly Thr Thr Tyr Phe Gln Pro
                165                 170                 175

Val Thr Glu Val Leu Ser Arg Tyr Gly Val Ser Val
            180                 185

<210> SEQ ID NO 40
<211> LENGTH: 189
<212> TYPE: PRT
<213> ORGANISM: Kribella aluminosa

<400> SEQUENCE: 40

Ile Ala Gly Gly Asp Ala Ile Tyr Gly Gly Gln Tyr Arg Cys Ser Leu
1               5                  10                  15

Gly Phe Asn Val Arg Ser Gly Ser Thr Tyr Tyr Phe Leu Thr Ala Gly
            20                  25                  30

His Cys Gly Asn Ile Ala Ser Ser Trp Tyr Ala Asn Ser Ser Lys Thr
        35                  40                  45

Thr Leu Leu Gly Thr Val Ala Gly Ser Ser Phe Pro Gly Asn Asp Tyr
    50                  55                  60

Ala Ile Val Arg Tyr Ser Thr Ser Tyr Thr Asn His Pro Gly Thr Val
65                  70                  75                  80

Asn Leu Tyr Asn Gly Ser Ser Gln Asp Ile Thr Ser Ala Gly Asn Ala
                85                  90                  95

Tyr Val Gly Gln Ala Val Lys Arg Ser Gly Ser Thr Thr Gly Val His
            100                 105                 110

Ser Gly Ser Val Thr Ala Thr Asn Ala Thr Val Asn Tyr Ala Glu Gly
```

```
              115                 120                 125
Thr Val Thr Gly Leu Ile Arg Thr Thr Val Cys Ala Glu Gly Gly Asp
        130                 135                 140

Ser Gly Gly Ala Leu Phe Ala Gly Thr Val Ala Leu Gly Leu Thr Ser
145                 150                 155                 160

Gly Gly Ser Gly Asn Cys Ser Ser Gly Thr Thr Tyr Phe Gln Pro
                165                 170                 175

Val Thr Glu Val Leu Ser Arg Tyr Gly Val Ser Val Tyr
        180                 185

<210> SEQ ID NO 41
<211> LENGTH: 160
<212> TYPE: PRT
<213> ORGANISM: Saccharomonospora viridis

<400> SEQUENCE: 41

Met Asp Val Ile Gly Gly Asn Ala Tyr Tyr Met Gly Asn Gly Gly Arg
1               5                   10                  15

Cys Ser Val Gly Phe Thr Val Gln Gly Gly Phe Val Thr Ala Gly His
            20                  25                  30

Cys Gly Thr Thr Gly Thr Ser Thr Ser Ser Pro Ser Gly Thr Phe Ala
        35                  40                  45

Gly Ser Ser Phe Pro Gly Asn Asp Tyr Ala Phe Val Arg Thr Gly Ser
    50                  55                  60

Gly Asp Thr Leu Arg Pro Trp Val Asn Met Tyr Asn Gly Ser Ala Arg
65                  70                  75                  80

Val Val Ser Gly Ser Ser Val Ala Pro Val Ser Ser Ile Cys Arg
            85                  90                  95

Ser Gly Ser Thr Thr Gly Trp His Cys Gly Gln Val Gln Ala Phe Asn
            100                 105                 110

Gln Thr Val Arg Tyr Ala Glu Gly Thr Val Thr Gly Leu Thr Arg Thr
            115                 120                 125

Asn Val Cys Ala Glu Pro Gly Asp Ser Gly Gly Ser Phe Ile Ser Gly
        130                 135                 140

Asn Gln Ala Gln Gly Met Thr Ser Gly Gly Ser Gly Asn Cys Thr Phe
145                 150                 155                 160

<210> SEQ ID NO 42
<211> LENGTH: 186
<212> TYPE: PRT
<213> ORGANISM: Saccharothrix australiensis

<400> SEQUENCE: 42

Ile Asp Val Ile Gly Gly Asn Ala Tyr Tyr Met Gly Ser Gly Gly Arg
1               5                   10                  15

Cys Ser Val Gly Phe Ser Val Asn Gly Gly Phe Val Thr Ala Gly His
            20                  25                  30

Cys Gly Arg Val Gly Thr Thr Thr Thr Gln Pro Ser Gly Thr Phe Ala
        35                  40                  45

Gly Ser Thr Phe Pro Gly Arg Asp Tyr Ala Trp Val Arg Val Ser Ser
    50                  55                  60

Gly Asn Thr Met Arg Gly Leu Val Asn Arg Tyr Pro Gly Thr Val Pro
65                  70                  75                  80

Val Lys Gly Ser Asn Glu Ser Ser Val Gly Ala Ser Val Cys Arg Ser
            85                  90                  95

Gly Ser Thr Thr Gly Trp His Cys Gly Thr Ile Gln Gln Lys Asn Thr
```

```
                100                 105                 110
Ser Val Thr Tyr Pro Glu Gly Thr Ile Ser Gly Val Thr Arg Thr Asn
            115                 120                 125

Ala Cys Ala Glu Pro Gly Asp Ser Gly Gly Ser Trp Leu Thr Gly Asp
        130                 135                 140

Gln Ala Gln Gly Val Thr Ser Gly Gly Ser Gly Asn Cys Ser Ser Gly
145                 150                 155                 160

Gly Thr Thr Tyr Phe Gln Pro Val Asn Pro Ile Leu Gln Ala Tyr Gly
                165                 170                 175

Leu Gln Leu Val Ile Glu Gly Gly Pro Thr
            180                 185

<210> SEQ ID NO 43
<211> LENGTH: 190
<212> TYPE: PRT
<213> ORGANISM: Saccharopolyspora erythraea

<400> SEQUENCE: 43

Tyr Asn Val Val Gly Gly Asp Ala Tyr Tyr Met Gly Gly Arg Cys Ser
1               5                   10                  15

Val Gly Phe Ser Val Arg Ser Ser Gly Gln Ala Gly Phe Val Thr
            20                  25                  30

Ala Gly His Cys Gly Thr Arg Gly Thr Ala Val Ser Gly Tyr Asn Gln
        35                  40                  45

Val Ala Met Gly Ser Phe Gln Gly Ser Ser Phe Pro Asn Asn Asp Tyr
    50                  55                  60

Ala Trp Val Ser Val Asn Ser Asn Trp Thr Pro Gln Pro Trp Val Asn
65                  70                  75                  80

Leu Tyr Asn Gly Ser Ala Arg Val Val Ser Gly Ser Ser Ala Ala Pro
                85                  90                  95

Val Gly Ser Ser Ile Cys Arg Ser Gly Ser Thr Thr Gly Trp His Cys
            100                 105                 110

Gly Ser Val Gln Ala Leu Asn Gln Thr Val Arg Tyr Ala Glu Gly Thr
        115                 120                 125

Val Tyr Gly Leu Thr Arg Thr Asn Val Cys Ala Glu Pro Gly Asp Ser
    130                 135                 140

Gly Gly Ser Phe Ile Ser Gly Asn Gln Ala Gln Gly Met Thr Ser Gly
145                 150                 155                 160

Gly Ser Gly Asn Cys Ser Ser Gly Gly Thr Thr Tyr Phe Gln Pro Val
                165                 170                 175

Asn Glu Ala Leu Ser Ala Tyr Gly Leu Ser Leu Val Arg Gly
            180                 185                 190

<210> SEQ ID NO 44
<211> LENGTH: 435
<212> TYPE: PRT
<213> ORGANISM: Bacillus sp NN019138

<400> SEQUENCE: 44

Val Thr Pro Asn Pro Thr Gly Arg Met Thr Asn Asp Leu Val Ser Arg
1               5                   10                  15

Tyr Asn Val Gln Pro Leu Tyr Thr Lys Gly Ala Asn Gly Ser Gly Gln
            20                  25                  30

Thr Ile Gly Ile Val Thr Leu Ala Asp Phe Asn Pro Ser Asp Ala Tyr
        35                  40                  45

Ser Tyr Trp Gln Tyr Asn Asn Ile Asn Val Asn Pro Asn Arg Ile Thr
```

```
            50                  55                  60
Lys Ile Asn Val Asp Gly Gly Ser Gly Leu Ser Glu Asp Ala Gly Ser
 65                  70                  75                  80

Asp Glu Thr Ser Leu Asp Val Glu Gln Ser Gly Ala Leu Ala Pro Gly
                 85                  90                  95

Ala Asn Leu Asn Val Tyr Val Gly Pro Asn Thr Asp Thr Gly Phe Val
            100                 105                 110

Asp Ala Tyr Ala Lys Ala Ile Asn Asp Asn Val Ala His Gln Ile Ser
            115                 120                 125

Ala Ser Trp Gly Glu Ser Glu Ser Leu Ile Asn Tyr Val Gln Gln
        130                 135                 140

Gln Met Glu Thr Pro Glu Tyr Ala Glu Thr Phe Asn Gln Leu Phe Met
145                 150                 155                 160

Gln Ala Ala Gln Gly Thr Ser Met Phe Ala Ser Ala Gly Asp Ser
                165                 170                 175

Gly Ala Tyr Asp Ala Ser Gly Asp Leu Asn Thr Tyr Asp Leu Ser Val
            180                 185                 190

Asp Asn Pro Ala Asp Ser Pro Tyr Ile Thr Ala Gly Gly Thr Thr
            195                 200                 205

Val Pro Phe Thr Tyr Thr Ser Thr Gln Tyr Asn Leu Ser Ile Thr Val
210                 215                 220

Pro Gln Glu Arg Ala Trp Gly Trp Asp Tyr Leu Tyr Pro Leu Phe Asp
225                 230                 235                 240

Ala Arg Gly Leu Asn Asn Pro Thr Gly Trp Ala Gln Arg Tyr Phe Val
                245                 250                 255

Gly Gly Gly Gly Gly Phe Ser Gln Leu Phe Ala Thr Pro Asp Tyr Gln
                260                 265                 270

Thr Gly Val Ser Gly Val Asn Ser Tyr Thr Ala Val His Gln Trp Thr
            275                 280                 285

Pro Ser Ser Asp Phe Thr Ser Val Thr Arg Asp Ala Gln Pro Thr Ile
290                 295                 300

Val Thr Gly Thr Gly Thr Gly Arg Asn Leu Pro Asp Leu Ser Met Asn
305                 310                 315                 320

Ala Asp Pro Tyr Thr Gly Tyr Ser Val Tyr Phe Asn Leu Pro Thr Thr
                325                 330                 335

Asn Gly Ala Thr Thr Val Asp Ser Gly Trp Ala Thr Tyr Gly Gly Thr
            340                 345                 350

Ser Phe Val Ala Pro Gln Leu Ala Gly Leu Ser Ala Leu Ile Asn Ser
            355                 360                 365

Ala Asn Gly Ser Glu Ala Gly Phe Trp Asn Pro Gln Leu Tyr Arg Phe
370                 375                 380

Ala Gln Ser Asn His Ser Pro Leu His Pro Leu Asn Thr Ala Gly Ala
385                 390                 395                 400

Ser Asn Asp Asn Val Phe Tyr Ser Gly Thr Pro Gly Ala Ile Tyr Asn
                405                 410                 415

Gln Ala Thr Gly Leu Gly Thr Pro Asp Val Thr Ala Leu Ala Gln Ala
            420                 425                 430

Phe Gly Lys
        435

<210> SEQ ID NO 45
<211> LENGTH: 183
<212> TYPE: PRT
<213> ORGANISM: Saccharopolyspora erythraea
```

<400> SEQUENCE: 45

Ala Asp Val Ile Gly Gly Asp Ala Tyr Tyr Ile Gly Ser Gly Ser Arg
1               5                   10                  15

Cys Ser Val Gly Phe Ser Val Gln Gly Gly Phe Val Thr Ala Gly His
            20                  25                  30

Cys Gly Asn Gln Gly Asp Ser Thr Ser Gln Pro Ser Gly Thr Phe Glu
        35                  40                  45

Gly Ser Ser Phe Pro Gly Asn Asp Tyr Gly Trp Val Arg Thr Ala Ser
    50                  55                  60

Gly Glu Asn Pro Val Pro Leu Val Asn Asp Tyr Gln Gly Gly Thr Val
65                  70                  75                  80

Gly Val Ala Gly Ser Ser Glu Ala Ala Glu Gly Ala Ser Ile Cys Arg
                85                  90                  95

Ser Gly Ser Thr Thr Gly Trp His Cys Gly Thr Val Glu Ala Lys Asn
            100                 105                 110

Gln Thr Val Arg Tyr Pro Gln Gly Thr Val Glu Gly Leu Thr Arg Thr
        115                 120                 125

Asn Val Cys Ala Glu Pro Gly Asp Ser Gly Gly Ser Trp Leu Ser Gly
130                 135                 140

Asp Gln Ala Gln Gly Val Thr Ser Gly Gly Ser Gly Asp Cys Thr Ser
145                 150                 155                 160

Gly Gly Thr Thr Tyr Phe Gln Pro Val Asn Glu Ile Leu Gln Ala Tyr
                165                 170                 175

Gly Leu Thr Leu Leu Thr Gln
            180

<210> SEQ ID NO 46
<211> LENGTH: 366
<212> TYPE: PRT
<213> ORGANISM: Meripilus giganteus

<400> SEQUENCE: 46

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
            20                  25                  30

Leu Ala Val Ser Gly Phe Ile Asp Gln Phe Ala Asn Lys Ala Asp Leu
        35                  40                  45

Lys Ser Phe Leu Ala Gln Phe Arg Lys Asp Ile Ser Ser Ser Thr Thr
    50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
        115                 120                 125

Glu Ser Asn Pro Pro Gln Val Leu Thr Thr Ser Tyr Gly Gln Asn Glu
    130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

```
Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
            195                 200                 205

Val Ser Pro Glu Thr Ala Ala Ala Phe Ser Ser Gly Gly Phe Ser Asn
210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
            245                 250                 255

Gly Phe Pro Asp Val Ser Thr Gln Gly Val Asp Phe Gln Ile Val Ser
            260                 265                 270

Gly Gly Gln Thr Ile Gly Val Asp Gly Thr Ser Cys Ala Ser Pro Thr
            275                 280                 285

Phe Ala Ser Val Ile Ser Leu Val Asn Asp Arg Leu Ile Ala Ala Gly
            290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
            325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
            355                 360                 365

<210> SEQ ID NO 47
<211> LENGTH: 187
<212> TYPE: PRT
<213> ORGANISM: Dactylosporangium variesporum

<400> SEQUENCE: 47

Ile Asp Val Ile Gly Gly Asn Ala Tyr Tyr Met Gly Gly Gly Gly Arg
1               5                   10                  15

Cys Ser Val Gly Phe Ser Val Asn Gly Gly Phe Val Thr Ala Gly His
            20                  25                  30

Cys Gly Thr Ser Gly Gln Ser Thr Thr Gln Pro Thr Gly Thr Phe Ala
            35                  40                  45

Gly Ser Ser Phe Pro Gly Asn Asp Tyr Ala Trp Val Arg Val Ala Ala
            50                  55                  60

Gly Asn Thr Pro Arg Gly Leu Val Asn Arg Tyr Pro Gly Thr Val Pro
65                  70                  75                  80

Val Ala Gly Ser Thr Glu Ala Pro Val Gly Ala Ser Val Cys Arg Ser
                85                  90                  95

Gly Ser Thr Thr Gly Trp His Cys Gly Thr Ile Gln Gln Arg Asn Thr
            100                 105                 110

Ser Val Thr Tyr Pro Gln Gly Thr Val Ser Gly Val Val Arg Thr Asn
            115                 120                 125

Ala Cys Ala Glu Pro Gly Asp Ser Gly Gly Ser Trp Ile Ser Gly Asp
            130                 135                 140

Gln Ala Gln Gly Val Thr Ser Gly Gly Ser Gly Asn Cys Ser Ser Gly
145                 150                 155                 160

Gly Thr Thr Tyr Phe Gln Pro Val Asn Glu Ile Leu Gln Ala Tyr Gly
                165                 170                 175

Leu Gln Leu Val Thr Ser Gly Gly Thr Pro Thr
            180                 185
```

```
<210> SEQ ID NO 48
<211> LENGTH: 275
<212> TYPE: PRT
<213> ORGANISM: Artificial Sequence
<220> FEATURE:
<223> OTHER INFORMATION: BPN' with mutation Y217L

<400> SEQUENCE: 48

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```